United States Patent
Moldenhauer

(10) Patent No.: US 8,431,805 B2
(45) Date of Patent: Apr. 30, 2013

(54) RICE CULTIVAR ROY J

(75) Inventor: Karen A. K. Moldenhauer, Stuttgart, AR (US)

(73) Assignee: Board of Trustees of the University of Arkansas, N.A., Little Rock, AR (US)

( * ) Notice: Subject to any disclaimer, the term of this patent is extended or adjusted under 35 U.S.C. 154(b) by 311 days.

(21) Appl. No.: 12/891,562

(22) Filed: Sep. 27, 2010

(65) Prior Publication Data

US 2012/0079619 A1   Mar. 29, 2012

(51) Int. Cl.
| | |
|---|---|
| *A01H 1/00* | (2006.01) |
| *A01H 5/00* | (2006.01) |
| *A01H 5/10* | (2006.01) |
| *A01H 1/02* | (2006.01) |
| *C12N 5/04* | (2006.01) |

(52) U.S. Cl.
USPC ........ 800/320.2; 800/260; 800/275; 800/278; 800/295; 800/298; 800/301; 800/302; 800/281; 435/410

(58) Field of Classification Search ................. None
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 6/1996 | Hunsperger et al. |
| 5,763,755 | A | 6/1998 | Carlone |
| 5,850,009 | A | 12/1998 | Kevern |
| 8,134,058 | B2 * | 3/2012 | Moldenhauer ............ 800/320.2 |

OTHER PUBLICATIONS

Bennetzen, et al., 1992, Approaches and progress in the molecular cloning of plant disease resistance genes, Genetic Engineering, 14:99-124.

DeBolle, et al., 1996, Antimicrobial peptides from *Mirabilis jalapa* and *Amaranthus caudatus*: expression, processing, localization and biological activity in transgenic tobacco, Plant Molec. Biol., 31:993-1008.

Eshed, et al., 1996, Less-than-additive epistatic interactions of quantitative trait loci in tomato, Genetics, 143:1807-1817.

Kraft, et al., 2000, Linkage disequilibrium and fingerprinting in sugar beet, Theor. Appl. Genet., 101:323-326.

Pang, et al., 1992, Expression of a gene encoding a scorpion insectotoxin peptide in yeast, bacteria and plants, Gene, 116:165-172.

Poehlman, J.M. and Sleper, D.A., Breeding Field Crops, 4th Ed. (1995), Iowa State University Press, p. 473.

Smith, C.W. and Dilday, R.H., Origin, Domestication, and Diversification in Rice: Origin, History, Technology, and Production, (2003), John Wiley & Sons, Inc., pp. 4-6.

Yu, et al., 1997, Importance of epistasis as the genetic basis of heterosis in an elite rice hybrid, Proc. Natl. Acad. Sci., 94:9226-9231.

US PVP Application No. 201100042 of The Board of Trustees of the University of Arkansas, N.A., filed Nov. 1, 2010.

* cited by examiner

*Primary Examiner* — Medina A Ibrahim

(74) *Attorney, Agent, or Firm* — Jondle Plant Sciences Division of Swanson & Bratschun, L.L.C.

(57) ABSTRACT

A rice cultivar designated Roy J is disclosed. The invention relates to the seeds of rice cultivar Roy J, to the plants of rice cultivar Roy J, to plant parts of rice cultivar Roy J, and to methods for producing a rice plant produced by crossing rice cultivar Roy J with itself or with another rice variety. The invention also relates to methods for producing a rice plant containing in its genetic material one or more transgenes and to the transgenic rice plants and plant parts produced by those methods. This invention also relates to rice cultivars, or breeding cultivars, and plant parts derived from rice cultivar Roy J, to methods for producing other rice cultivars, lines or plant parts derived from rice cultivar Roy J, and to the rice plants, varieties, and their parts derived from use of those methods. The invention further relates to hybrid rice seeds, plants, and plant parts produced by crossing rice cultivar Roy J with another rice cultivar.

22 Claims, No Drawings

RICE CULTIVAR ROY J

BACKGROUND OF THE INVENTION

The present invention relates to a new and distinctive rice cultivar, designated Roy J. All publications cited in this application are herein incorporated by reference.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 cm to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Long-grain cultivars have been traditionally grown in the southern states and generally receive higher market prices.

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics or grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior crosses. The $F_1$ seed is produced by manual crosses between selected male-fertile parents or by using male sterility systems. These $F_1$s are selected for certain single gene traits such as semi-dwarf plant type, pubescence, awns, and apiculus color which indicate that the seed is truly a hybrid. Additional data on parental lines, as well as the phenotype of the $F_1$, influence the breeder's decision whether to continue with the specific cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep, et. al, 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Rice, *Oryza sativa* L., is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel rice cultivar designated 'Roy J'. This invention thus relates to the seeds of rice cultivar Roy J, to the plants of rice Roy J, and to methods for producing a rice plant produced by crossing rice Roy J with itself or another rice line.

Thus, any such methods using rice variety Roy J are part of this invention: selfing, backcrosses, hybrid production, crosses to populations, and the like. All plants produced using rice variety Roy J as a parent are within the scope of this invention. Advantageously, the rice variety could be used in crosses with other, different, rice plants to produce first generation ($F_1$) rice hybrid seeds and plants with superior characteristics.

In another aspect, the present invention provides for single gene converted plants of Roy J. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant Roy J. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, pistils, root tips, flowers, seeds, panicles, or stems. Still further, the present invention provides rice plants regenerated from the tissue cultures of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Alkali Spreading Value. Indicator of gelatinization temperature and an index that measures the extent of disintegration of milled rice kernel in contact with dilute alkali solution. Standard long grains have 3 to 5 Alkali Spreading Value (intermediate gelatinization temperature).

Allele. Allele is any of one or more alternative forms of a gene, all of which relate to one trait or characteristic. In a diploid cell or organism, the two alleles of a given gene occupy corresponding loci on a pair of homologous chromosomes.

Apparent Amylose Percent. The most important grain characteristic that describes cooking behavior in each grain class, or type, i.e., long-, medium- and short-grain. The percentage of the endosperm starch of milled rice that is amylose. Standard long grains contain 20% to 23% amylose. Rexmont type long grains contain 24% to 25% amylose. Short and medium grains contain 16% to 19% amylose. Waxy rice contains 0% amylose. Amylose values will vary over environments.

Backcrossing. Backcrossing is a process in which a breeder repeatedly crosses hybrid progeny back to one of the parents, for example, a first generation hybrid $F_1$ with one of the parental genotypes of the $F_1$ hybrid.

Days to 50% heading. Average number of days from emergence to the day when 50% of all panicles are exerted at least partially through the leaf sheath. A measure of maturity.

Essentially all the physiological and morphological characteristics. A plant having essentially all the physiological and morphological characteristics means a plant having the physiological and morphological characteristics of the cultivar, except for the characteristics derived from the converted gene.

Grain Length (L). Length of a rice grain is measured as millimeters.

Grain Width (W). Width of a rice grain is measured as millimeters.

Grain Yield. Grain yield is measured in pounds per acre and at 12.0% moisture. Grain yield of rice is determined by the number of panicles per unit area, the number of fertile florets per panicle, and grain weight per floret.

Harvest Moisture. The percent of moisture of the grain when harvested.

Length/Width (L/W) Ratio. This ratio is determined by dividing the average length (L) by the average width (W).

Lodging Resistance (also called Straw Strength). Lodging is measured as a subjective rating and is percentage of the plant stems leaning or fallen completely to the ground before harvest. Relative scale.

1000 Grain Wt. The weight of 1000 rice grains as measured in grams.

Plant Height. Plant height in centimeters is taken from soil surface to the tip of the extended panicle at harvest.

Peak Viscosity. The maximum viscosity attained during heating when a standardized instrument-specific protocol is applied to a defined rice flour-water slurry.

Trough Viscosity. The minimum viscosity after the peak, normally occurring when the sample starts to cool.

Final Viscosity. Viscosity at the end of the test or cold paste.

Breakdown. The peak viscosity minus the hot paste viscosity.

Setback. Setback 1 is the final viscosity minus trough viscosity. Setback 2 is the final viscosity minus peak viscosity.

RVA Viscosity. Rapid Visco Analyzer is a widely used laboratory instrument to examine paste viscosity, or thickening ability of milled rice during the cooking process.

Hot Paste Viscosity. Viscosity measure of rice flour/water slurry after being heated to 95° C. Lower values indicate softer and stickier cooking types of rice.

Cool Paste Viscosity. Viscosity measure of rice flour/water slurry after being heated to 95° C. and uniformly cooled to 50° C. (American Association of Cereal Chemist). Values less than 200 for cool paste indicate softer cooking types of rice.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

Roy J originated from the cross 'LaGrue'//'Katy'/'Starbonnet'/5/'Newbonnet'/Katy//RA73/'Lemont'/4/'Lebonnet'/CI9902/3/'Dawn'/CI9695//Starbonnet, made at the Rice Research and Extension Center, in Stuttgart, Ark., in 2000. Roy J is a very high yielding, mid-season, long-grain rice cultivar with a similar maturity to rice cultivar Drew. Plants of Roy J have erect culms, dark-green erect leaves, and glaborus lemma, palea, and leaf blades. The lemma and palea are straw colored with red and purple apiculi, many of which fade to straw at maturity. Roy J is partially awned with long awns on the lemma when grown under high fertility. Kernels of rice cultivar Roy J are similar to size to Cybonnet. Individual milled kernel weights (in milligrams) of rice cultivar Roy J, Francis, Wells, LaGrue, Cybonnet, Cocodrie, and Drew averaged 18.3, 17.3, 18.9, 17.8, 17.7, 17.8, and 15.9, respectively, in the Arkansas Rice Performance Trials (ARPT) from 2007 to 2009.

Roy J is a standard height long grain rice cultivar similar to Wells in appearance with high yield potential and very good lodging resistance. Roy J has better straw strength than Francis or Wells which is an indicator of lodging resistance. On a relative straw strength scale (0=very strong straw, 9=very weak straw) Roy J, Francis, Wells, LaGrue, Drew, Cybonnet and Cocodrie rated 2, 4, 3, 5, 6, 2, and 2, respectively. Roy J is 110 cm in plant height which is similar to Taggart and LaGrue.

Rough rice grain yields of Roy J have consistently ranked as one of the highest in the ARPT. In 12 ARPT tests conducted from 2007 to 2009, Roy J, Taggart, Francis, Wells, Cybonnet, Cocodrie, and Drew averaged yields of 9677, 9223, 9122, 8971, 8014, 7711, and 8215 kg ha$^{-1}$ (120 g kg$^{-1}$ (12%) moisture), respectively. Data from the Uniform Regional Rice Nursery (URRN) conducted in Arkansas, Louisiana, Mississippi, Missouri and Texas during 2008 to 2009, showed that Roy J average grain yield of 10,452 kg ha$^{-1}$ compared favorably with those of Taggart, Francis, Wells, Cybonnet, and Cocodrie, at 10,416, 9559, 9866, 9167 and 9725 kg ha$^{-1}$, respectively. Milling yields (mg g$^{-1}$ whole kernel:mg g$^{-1}$ total milled rice) at 120 mg g$^{-1}$ moisture from the ARPT conducted from 2007 to 2009, averaged 590:710, 580:720, 610:710, 550:720, 570:700, 640:720, 640:710, and 590:710, for Roy J, Taggart, Francis, Wells, LaGrue, Cybonnet, Cocodrie, and Drew, respectively. Milling yields for the URRN during the same period of time, from 2008 to 2009 (without Missouri in 2008), averaged 580:720, 570:720, 590:710, 590:720, 650:730, and 630:720, for Roy J, Taggart, Francis, Wells, Cybonnet, and Cocodrie, respectively.

The cultivar has shown uniformity and stability as described in the following variety description information. It has been self-pollinated a sufficient number of generations with careful attention to uniformity of plant type. The variety has been increased with continued observation for uniformity.

Rice cultivar Roy J has the following morphologic and other characteristics (based primarily on data collected in Stuttgart, Ark.).

TABLE 1

VARIETY DESCRIPTION INFORMATION

| | |
|---|---|
| Plant: | |
| Grain type: | Long |
| Days to maturity (50% heading): | 96 (range is 84 to 104 days) |
| Plant height: | 110 cm (range is 95 cm to 120 cm) |
| Plant color (at booting): | Dark Green |

TABLE 1-continued

VARIETY DESCRIPTION INFORMATION

| | |
|---|---|
| Culm: | |
| Angle (degrees from perpendicular after flowering): | Erect (<30 degrees) |
| Flag leaf (after heading): | |
| Pubescence: | Glabrous |
| Leaf angle (after heading): | Erect |
| Blade color: | Dark Green |
| Panicle: | |
| Length: | 30.3 cm (range is 24-43 cm) |
| Type: | Intermediate |
| Exsertion (near maturity): | 99% to 100% Moderately well |
| Axis: | Droopy |
| Shattering: | Low (1% to 5%) |
| Grain (Spikelet): | |
| Awns (after full heading): | Partially awned; awns can be absent, short or long (effected by environment can range from a few awns to many in field) |
| Apiculus color (at maturity): | Purple |
| Stigma color: | White and purple |
| Lemma and palea color (at maturity): | Straw |
| Lemma and palea pubescence: | Glabrous |
| Grain (Seed): | |
| Seed coat (bran) color: | Light-brown |
| Endosperm type: | Nonglutinous |
| Scent: | Nonscented |
| Shape class (length/width ratio): | |
| Paddy: | Long 3.4:1 and more |
| Brown: | Long 3.1:1 and more |
| Milled: | Long 3.0:1 and more |
| Size: | 18.5 mg/seed milled rice |
| Starch amylose content: | 22.4 g kg$^{-1}$ |
| Alkali spreading value: | 3 to 5 (17 g kg$^{-1}$ KOH Solution) |
| Gelatinization temperature type: | Intermediate (70° C. to 75° C.) |
| Disease Resistance: | |
| Rice blast (*Pyricularia grisea* (Cooke) Sacc.): | Susceptible |
| Straighthead (*Oebalus pugnax*): | Susceptible |
| Narrow brown leaf spot (*Cercospora oryzae* Miyake): | Moderately susceptible |
| Kernel smut (*Tilletia barclayana* (Bref.) Sacc. & Syd. in Sacc.): | Susceptible under high nitrogen fertilization |
| Brown spot (*Cochliobolus miyabeanus*): | Resistant under recommended potassium fertilization levels |
| Stem rot (*Sclerotium oryzae*): | Susceptible |
| Sheath blight (*Rhizoctonia solani* Kühn): | Moderately susceptible |
| False smut (*Ustilaginoidea virens*): | Susceptible under high nitrogen fertilization |
| Crown (black) sheath rot: | Moderately susceptible |
| Bacterial panicle blight: | Susceptible |

This invention also is directed to methods for producing a rice plant by crossing a first parent rice plant with a second parent rice plant wherein either the first or second parent rice plant is a rice plant of the line Roy J. Further, both first and second parent rice plants can come from the rice cultivar Roy J. Still further, this invention also is directed to methods for producing a rice cultivar Roy J-derived rice plant by crossing rice cultivar Roy J with a second rice plant and growing the progeny seed, and repeating the crossing and growing steps with the rice cultivar Roy J-derived plant from 0 to 7 times. Thus, any such methods using the rice cultivar Roy J are part of this invention: selfing, backcrosses, hybrid production, crosses to populations, and the like. All plants produced using rice cultivar Roy J as a parent are within the scope of this invention, including plants derived from rice cultivar Roy J. Advantageously, the rice cultivar is used in crosses with other, different, rice cultivars to produce first generation ($F_1$) rice seeds and plants with superior characteristics.

It should be understood that the cultivar can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

Further Embodiments of the Invention

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol. Rep.*, 5:387 (1987); Teeri, et al., *EMBO J.*, 8:343 (1989); Koncz, et al., *Proc. Natl. Acad. Sci. U.S.A.*, 84:131 (1987); DeBlock, et al., *EMBO J.*, 3:1681 (1984). Another approach to the identification of relatively rare transformation events has been use of a gene that encodes a dominant constitutive regulator of the *Zea mays* anthocyanin pigmentation pathway. Ludwig, et al., *Science*, 247:449 (1990).

In vivo methods for visualizing GUS activity that do not require destruction of plant tissue are available. Molecular Probes Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263: 802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See, Ward, et al., *Plant Mol. Biol.*, 22:361-366 (1993). Exemplary inducible promoters include, but are not limited to, that from the ACEI system which responds to copper (Meft, et al., *PNAS*, 90:4567-4571 (1993)); In2 gene from maize which responds to benzenesulfonamide herbicide safeners (Hershey, et al., *Mol. Gen. Genetics,* 227:229-237 (1991) and Gatz, et al., *Mol. Gen. Genetics,* 243:32-38 (1994)) or Tet repressor from Tn10 (Gatz, et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *Proc. Natl. Acad. Sci. U.S.A.,* 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell,* 2:163-171 (1990)); ubiquitin (Christensen, et al., *Plant Mol. Biol.,* 12:619-632 (1989) and Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)); and maize H3 histone (Lepetit, et al., *Mol. Gen. Genetics,* 231: 276-285 (1992) and Atanassova, et al., *Plant Journal* 2 (3): 291-300 (1992)).

The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See, PCT Appl. No. WO 96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science,* 23:476-482 (1983) and Sengupta-Gopalan, et al., *Proc. Natl. Acad. Sci. USA.,* 82:3320-3324 (1985)); a leaf-specific and light-induced promoter such as that from cab or rubisco (Simpson, et al., *EMBO J.,* 4(11): 2723-2729 (1985) and Timko, et al., *Nature,* 318:579-582 (1985)); an anther-specific promoter such as that from LAT52 (Twell, et al., *Mol. Gen. Genetics,* 217:240-245 (1989)); a pollen-specific promoter such as that from Zm13 (Guerrero, et al., *Mol. Gen. Genetics,* 244:161-168 (1993)) or a microspore-preferred promoter such as that from apg (Twell, et al., *Sex. Plant Reprod.,* 6:217-224 (1993)).

Signal Sequences for Targeting Proteins to Sub-cellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Close, P. S., Master's Thesis, Iowa State University (1993); Knox, C., et al., *Plant Mol. Biol.,* 9:3-17 (1987); Lerner, et al., *Plant Physiol.,* 91:124-129 (1989); Fontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., *Plant Cell,* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecular Biology and Biotechnology,* Glick and Thompson Eds., CRC Press, Inc., Boca Raton, pp. 269-284 (1993)). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Through the transformation of rice, the expression of genes can be altered to enhance disease resistance, insect resistance, herbicide resistance, agronomic quality and other traits. Transformation can also be used to insert DNA sequences which control or help control male-sterility. DNA sequences native to rice as well as non-native DNA sequences can be transformed into rice and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well-known to one of skill in the art, including, but not limited to, knock-outs (such as by insertion of a transposable element such as mu (Vicki Chandler, The Maize Handbook, ch. 118, Springer-Verlag (1994)) or other genetic elements such as a FRT, Lox, or other site specific integration site, antisense technology (see, e.g., Sheehy, et al., *PNAS USA,* 85:8805-8809 (1988); and U.S. Pat. Nos. 5,107,065; 5,453,566; and 5,759,829); co-suppression (e.g., Taylor, *Plant Cell,* 9:1245 (1997); Jorgensen, *Trends Biotech.*, 8(12):340-344 (1990); Flavell, *PNAS USA*, 91:3490-3496 (1994); Finnegan, et al., *Bio/Technology*, 12: 883-888 (1994); and Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); and Montgomery, et al., *PNAS USA*, 95:15502-15507 (1998)); virus-induced gene silencing (Burton, et al., *Plant Cell*, 12:691-705 (2000); and Baulcombe, *Curr. Op. Plant Bio.*, 2:109-113 (1999)); target-RNA-specific ribozymes (Haseloff, et al., *Nature*, 334: 585-591 (1988)); hairpin structures (Smith, et al., *Nature*, 407:319-320 (2000); WO 99/53050; and WO 98/53083); MicroRNA (Aukerman & Sakai, *Plant Cell*, 15:2730-2741 (2003)); ribozymes (Steinecke, et al., *EMBO J.*, 11:1525 (1992); and Perriman, et al., *Antisense Res. Dev.*, 3:253 (1993)); oligonucleotide mediated targeted modification (e.g., PCT Publication Nos. WO 03/076574 and WO 99/25853); Zn-finger targeted molecules (e.g., PCT Publication Nos. WO 01/52620; WO 03/048345; and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. tomato encodes a protein kinase); Mindrinos, et al., *Cell*, 78:1089 (1994) (*Arabidopsis* RSP2 gene for resistance to *Pseudomonas syringae*); McDowell & Woffenden, *Trends Biotechnol.*, 21(4): 178-83 (2003); and Toyoda, et al., *Transgenic Res.*, 11 (6):567-82 (2002).

B. A *Bacillus thuringiensis* protein, a derivative thereof or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, the disclosure by Van Damme, et al., *Plant Molec. Biol.*, 24:25 (1994), who disclose the nucleotide sequences of several *Clivia miniata* mannose-binding lectin genes.

D. A vitamin-binding protein such as avidin. See, PCT Appl. No. US 93/06487. The application teaches the use of avidin and avidin homologues as larvicides against insect pests.

E. An enzyme inhibitor, for example, a protease or proteinase inhibitor or an amylase inhibitor. See, for example, Abe, et al., *J. Biol. Chem.*, 262:16793 (1987) (nucleotide sequence of rice cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor), and Pratt, et al., *Biochem. Biophys. Res. Comm.*, 163:1243 (1989) (an allostatin is identified in *Diploptera puntata*). See also, U.S. Pat. No. 5,266,317 to Tomalski, et al., who disclose genes encoding insect-specific, paralytic neurotoxins.

H. An insect-specific venom produced in nature by a snake, a wasp, etc. For example, see Pang, et al., *Gene*, 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Publication No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., Insect *Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene.

K. A molecule that stimulates signal transduction. For example, see the disclosure by Botella, et al., *Plant Molec. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

L. A hydrophobic moment peptide. See, PCT Publication No. WO 95/16776 (disclosure of peptide derivatives of Tachyplesin which inhibit fungal plant pathogens) and PCT Publication No. WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes, et al., *Plant Sci*, 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor, et al., Abstract #497, Seventh International Symposium on Molecular Plant-Microbe Interactions (Edinburgh, Scotland (1994)) (enzymatic inactivation in transgenic tobacco via production of single-chain antibody fragments).

P. A virus-specific antibody. See, for example, Tavladoraki, et al., Nature, 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., Bio/Technology, 10:1436 (1992). The cloning and characterization of a gene which encodes a bean endopolygalacturonase-inhibiting protein is described by Toubart, et al., Plant J., 2:367 (1992).

R. A developmental-arrestive protein produced in nature by a plant. For example, Logemann, et al., Bio/Technology, 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., Current Biology, 5(2) (1995); Pieterse & Van Loon, Curr. Opin. Plant Bio., 7(4):456-64 (2004) and Somssich, Cell, 113(7):815-6 (2003).

T. Antifungal genes. See, Cornelissen and Melchers, Plant Physiol., 101:709-712 (1993); Parijs, et al., Planta, 183:258-264 (1991) and Bushnell, et al., Can. J. of Plant Path., 20(2): 137-149 (1998). See also, U.S. Pat. No. 6,875,907.

U. Detoxification genes, such as for fumonisin, beauvericin, moniliformin, and zearalenone, and their structurally related derivatives. For example, see U.S. Pat. No. 5,792,931.

V. Cystatin and cysteine proteinase inhibitors. See U.S. Pat. No. 7,205,453.

W. Defensin genes. See PCT Publication No. WO 03/000863 and U.S. Pat. No. 6,911,577.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., EMBO J., 7:1241 (1988) and Miki, et al., Theor. Appl. Genet., 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and Streptomyces hygroscopicus PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Pat. Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Pat. Appl. No. 0 242 246 to Leemans, et al. DeGreef, et al., Bio/Technology, 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2, and Acc1-S3 genes described by Marshall, et al., Theor. Appl. Genet., 83:435 (1992).

C. An herbicide that inhibits photosynthesis, such as a triazine (psbA and gs+ genes) or a benzonitrile (nitrilase gene). Przibilla, et al., Plant Cell, 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., Biochem. J., 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., Proc. Natl. Acad. Sci. U.S.A., 89:2624 (1992).

B. Decreased phytate content. 1) Introduction of a phytase-encoding gene would enhance breakdown of phytate, adding more free phosphate to the transformed plant. For example, see, Van Hartingsveldt, et al., Gene, 127:87 (1993), for a disclosure of the nucleotide sequence of an Aspergillus niger phytase gene; 2) A gene could be introduced that reduced phytate content. In maize, this, for example, could be accomplished by cloning and then reintroducing DNA associated with the single allele which is responsible for maize mutants characterized by low levels of phytic acid. See, Raboy, et al., Maydica, 35:383 (1990).

C. Modified carbohydrate composition effected, for example, by transforming plants with a gene coding for an enzyme that alters the branching pattern of starch. See, Shiroza, et al., J. Bacteol., 170:810 (1988) (nucleotide sequence of Streptococcus mutants fructosyltransferase gene); Steinmetz, et al., Mol. Gen. Genet., 20:220 (1985) (nucleotide sequence of Bacillus subtilis levansucrase gene); Pen, et al., Bio/Technology, 10:292 (1992) (production of transgenic plants that express Bacillus licheniformis α-amylase); Elliot, et al., Plant Molec. Biol., 21:515 (1993) (nucleotide sequences of tomato invertase genes); Søgaard, et al., J. Biol. Chem., 268:22480 (1993) (site-directed mutagenesis of barley α-amylase gene); and Fisher, et al., Plant Physiol., 102: 1045 (1993) (maize endosperm starch branching enzyme II).

4. Genes that Control Male Sterility:

There are several available methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432, 068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. A tapetum-specific gene, RTS, a rice anther-specific gene is required for male fertility and its promoter sequence directs tissue-specific gene expression in different plant species. Luo, Hong, et. al., *Plant Molecular Biology.*, 62(3): 397-408(12) (2006). Introduction of a deacetylase gene under the control of a tapetum-specific promoter and with the application of the chemical N-Ac-PPT. See PCT Publication No. WO 01/29237.

B. Introduction of various stamen-specific promoters. Rice anther-specific promoters which are of particular utility in the production of transgenic male-sterile monocots and plants for restoring their fertility. See, U.S. Pat. No. 5,639,948. See also, PCT Publication Nos. WO 92/13956 and WO 92/13957.

C. Introduction of the barnase and the barstar genes. See, Paul, et al., *Plant Mol. Biol.*, 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640. See also, Hanson, Maureen R., et. al., "Interactions of Mitochondrial and Nuclear Genes That Affect Male Gametophyte Development," *Plant Cell.*, 16:S154-S169 (2004), all of which are hereby incorporated by reference.

5. Genes that Create a Site for Site Specific DNA Integration:

This includes the introduction of FRT sites that may be used in the FLP/FRT system and/or Lox sites that may be used in the Cre/Loxp system. For example, see, Lyznik, et al., Site-Specific Recombination for Genetic Engineering in Plants, *Plant Cell Rep*, 21:925-932 (2003) and PCT Publication No. WO 99/25821, which are hereby incorporated by reference. Other systems that may be used include the Gin recombinase of phage Mu (Maeser, et al. (1991); Vicki Chandler, The Maize Handbook, ch. 118, Springer-Verlag (1994), the Pin recombinase of *E. coli* (Enomoto, et al. (1983)), and the R/RS system of the pSR1 plasmid (Araki, et al. (1992)).

6. Genes that Affect Abiotic Stress Resistance:

Genes that affect abiotic stress resistance (including, but not limited to, flowering, panicle/glume and seed development, enhancement of nitrogen utilization efficiency, altered nitrogen responsiveness, drought resistance or tolerance, cold resistance or tolerance, and salt resistance or tolerance) and increased yield under stress. For example, see: Xiong, Lizhong, et al., "Disease Resistance and Abiotic Stress Tolerance in Rice Are Inversely Modulated by an Abscisic Acid-Inducible Mitogen-Activated Protein Kinase," *The Plant Cell.*, 15:745-759 (2003), where OsMAPK5 can positively regulate drought, salt, and cold tolerance and negatively modulate PR gene expression and broad-spectrum disease resistance in rice; Chen, Fang, et. al., "The Rice 14-3-3 Gene Family and its Involvement in Responses to Biotic and Abiotic Stress," *DNA Research*, 13(2):53-63 (2006), where at least four rice GF14 genes, GF14b, GF14c, GF14e, and Gfl4f, were differentially regulated by salinity, drought, wounding, and abscisic acid; PCT Publication No. WO 00/73475 where water use efficiency is altered through alteration of malate; U.S. Pat. Nos. 5,892,009, 5,965,705, 5,929,305, 5,891,859, 6,417,428, 6,664,446, 6,717,034, and 6,801,104, and PCT Publication Nos. WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publication No. 2004/0148654 and PCT Publication No. WO 01/36596 where abscisic acid is altered in plants resulting in improved plant phenotype such as increased yield and/or increased tolerance to abiotic stress; PCT Publication Nos. WO 2000/006341 and WO 04/090143, U.S. Publication No. 2004/0237147, and U.S. Pat. No. 6,992, 237, where cytokinin expression is modified resulting in plants with increased stress tolerance, such as drought tolerance and/or increased yield. Also see, PCT Publication Nos. WO 02/02776, WO 2003/052063, WO 01/64898, JP 2002281975, and U.S. Pat. Nos. 6,084,153, 6,177,275, and 6,107,547 (enhancement of nitrogen utilization and altered nitrogen responsiveness). For ethylene alteration, see, U.S. Publication Nos. 2004/0128719 and 2003/0166197 and PCT Publication No. WO 2000/32761. For plant transcription factors or transcriptional regulators of abiotic stress, see, e.g., U.S. Publication Nos. 2004/0098764 and 2004/0078852.

Other genes and transcription factors that affect plant growth and agronomic traits such as yield, flowering, plant growth, and/or plant structure, can be introduced or introgressed into plants, see, e.g., PCT Publication Nos. WO 97/49811 (LHY), WO 98/56918 (ESD4), WO 97/10339, WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), and U.S. Pat. Nos. 6,573,430 (TFL), 6,713,663 (FT), 6,794,560, 6,307, 126 (GAI), and PCT Publication Nos. WO 2004/076638 and WO 2004/031349 (transcription factors).

Methods for Rice Transformation

Numerous methods for plant transformation have been developed, including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993)). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,591,616, issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei, et al., *The Plant Journal*, 6:271-282 (1994) and U.S. Pat. No. 5,591,616, issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Technology*, 6:559-563 (1988); Sanford, J. C., *Physiol Plant*, 7:206 (1990); Klein, et al., *Biotechnology*, 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang, et al., *Bio/Technology*, 9:996 (1991). Additionally, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994).

Following transformation of rice target tissues, expression of the above-described selectable marker genes allows for preferential selection of transformed cells, tissues, and/or plants using regeneration and selection methods now well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), which are also referred to as Microsatellites, and Single Nucleotide Polymorphisms (SNPs). For example, see, Cregan et. al, "An Integrated Genetic Linkage Map of the Soybean Genome," *Crop Science*, 39:1464-1490 (1999), and Berry, et al., Assessing Probability of Ancestry Using Simple Sequence Repeat Profiles: Applications to Maize Inbred Lines and Soybean Varieties," *Genetics*, 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for rice cultivar Roy J.

Primers and PCR protocols for assaying these and other markers are widely known in the art. In addition to being used for identification of rice cultivar Roy J and plant parts and plant cells of rice cultivar Roy J, the genetic profile may be used to identify a rice plant produced through the use of rice cultivar Roy J or to verify a pedigree for progeny plants produced through the use of rice cultivar Roy J. The genetic marker profile is also useful in breeding and developing backcross conversions.

The present invention comprises a rice cultivar plant characterized by molecular and physiological data obtained from the representative sample of said cultivar deposited with the American Type Culture Collection (ATCC). Further provided by the invention is a rice hybrid plant formed by the combination of the disclosed rice plant or plant cell with another rice plant or cell.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing hybrids or varieties it is preferable if all SSR profiles are performed in the same lab.

Primers used are publicly available and may be found in for example in U.S. Pat. Nos. 7,232,940, 7,217,003, 7,250,556, 7,214,851, 7,195,887, and 7,192,774.

In addition, plants and plant parts substantially benefiting from the use of rice cultivar Roy J in their development, such as rice cultivar Roy J comprising a backcross conversion, transgene, or genetic sterility factor, may be identified by having a molecular marker profile with a high percent identity to rice cultivar Roy J. Such a percent identity might be 95%, 96%, 97%, 98%, 99%, 99.5%, or 99.9% identical to rice cultivar Roy J.

The SSR profile of rice cultivar Roy J also can be used to identify essentially derived varieties and other progeny varieties developed using rice cultivar Roy J, as well as cells and other plant parts thereof. Such plants may be developed using the markers identified in International Publication No. WO 00/31964, U.S. Pat. No. 6,162,967, and U.S. application Ser. No. 09/954,773. Progeny plants and plant parts produced using rice cultivar Roy J may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from a rice hybrid or variety, as measured by either percent identity or percent similarity. Such progeny may be further characterized as being within a pedigree distance of rice cultivar Roy J, such as within 1, 2, 3, 4, or 5 or fewer cross-pollinations to a rice plant other than rice cultivar Roy J or a plant that has rice cultivar Roy J as a progenitor. Unique molecular profiles may be identified with other molecular tools such as SNPs and RFLPs.

While determining the SSR genetic marker profile of the plants described supra, several unique SSR profiles may also be identified which did not appear in either parent of such rice plant. Such unique SSR profiles may arise during the breeding process from recombination or mutation. A combination of several unique alleles provides a means of identifying a plant variety, an $F_1$ progeny produced from such variety, and progeny produced from such rice plan.

The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Gene Conversion

When the term "rice plant" is used in the context of the present invention, this also includes any gene conversions of that cultivar. The term gene converted plant as used herein refers to those rice plants which are developed by a plant breeding technique called backcrossing wherein essentially all of the desired morphological and physiological characteristics of a cultivar are recovered in addition to the one or more genes transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9, or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper (1994); Fehr (1987)). In a typical backcross protocol, the original cultivar of interest (recurrent parent) is crossed to a second cultivar (nonrecurrent parent) that carries the single gene or genes of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to one or more transferred genes from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, one or more genes of the recurrent cultivar is modified or substituted with the desired gene or genes from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196, 5,948,957, and 5,969,212, the disclosures of which are specifically hereby incorporated by reference.

Introduction of a New Trait or Locus into Rice Cultivar Roy J

Rice cultivar Roy J represents a new base genetic hybrid into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Rice Cultivar Roy J

A backcross conversion of rice cultivar Roy J occurs when DNA sequences are introduced through backcrossing (Hallauer, et al., "Corn Breeding," *Corn and Corn Improvements*, No. 18, pp. 463-481 (1988)), with rice cultivar Roy J utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, in: *Proceedings Symposium of the Analysis of Molecular Data, Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as vs unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See, Hallauer, et al., in *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments of the invention, the number of loci that may be backcrossed into rice cultivar Roy J is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site specific integration system allows for the integration of multiple genes at the converted loci.

Tissue Culture

Further reproduction of the variety can occur by tissue culture and regeneration. Tissue culture of various tissues of rice and regeneration of plants therefrom is well known and widely published. For example, reference may be had to Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992); as well as U.S. Pat. No. 5,024,944, issued Jun. 18, 1991 to Collins, et al., and U.S. Pat. No. 5,008,200, issued Apr. 16, 1991 to Ranch, et al. Thus, another aspect of this invention is to provide cells which upon growth and differentiation produce rice plants having the physiological and morphological characteristics of rice variety Roy J.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234, and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, pistils, anthers, and the like. Thus, another aspect of this invention is to provide for cells which upon growth and differentiation produce a cultivar having essentially all of the physiological and morphological characteristics of Roy J.

The present invention contemplates a rice plant regenerated from a tissue culture of a variety (e.g., Roy J) or hybrid plant of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., "Use of bridging parents with high anther culturability to improve plant regeneration and breeding value in rice," *Rice Biotechnology Quarterly*, 38:25-26 (1999); Chu, Q. R., et al., "A novel plant regeneration medium for rice anther culture of Southern U.S. crosses," *Rice Biotechnology Quarterly*, 35:15-16 (1998); Chu, Q. R., et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J. Breed.*, 33 (Suppl. 2), 306-307, illus. 1983. Thus, another aspect of this invention is to provide cells which upon growth and differentiation produce rice plants having the physiological and morphological characteristics of variety Roy J. Duncan, et al., *Planta*, 165:322-332 (1985), reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports*, 7:262-265 (1988), reports several media additions that enhance regenerability of callus of two cultivars. Other published reports also indicated that "non-traditional" tissues are capable of producing somatic embryogenesis and plant regeneration. K. P. Rao, et al., *Maize Genetics Cooperation Newsletter*, 60:64-65 (1986), refers to somatic embryogenesis from glume callus cultures and B. V. Conger, et al., *Plant Cell Reports*, 6:345-347 (1987), indicates somatic embryogenesis from the tissue cultures of corn leaf segments. Thus, it is clear from the literature that the state of the art is such that these methods of obtaining plants are routinely used and have a very high rate of success.

Tissue culture of corn is described in European Patent Application Publication 160,390. Corn tissue culture procedures are also described in Green and Rhodes, "Plant Regeneration in Tissue Culture of Maize," *Maize for Biological Research*, Plant Molecular Biology Association, Charlottesville, Va., 367-372 (1982), and in Duncan, et al., "The Production of Callus Capable of Plant Regeneration from Immature Embryos of Numerous *Zea Mays* Genotypes," 165 *Planta*, 322:332 (1985). Thus, another aspect of this invention is to provide cells which upon growth and differentiation produce corn plants having the physiological and morphological characteristics of rice cultivar Roy J.

The utility of rice cultivar Roy J also extends to crosses with other species. Commonly, suitable species will be of the family Graminaceae, and especially of the genera *Zea, Tripsacum, Croix, Schlerachne, Polytoca, Chionachne*, and *Trilobachne*, of the tribe Maydeae.

This invention also is directed to methods for producing a rice plant by crossing a first parent rice plant with a second parent rice plant wherein the first or second parent rice plant is a rice plant of the variety Roy J. Further, both first and second parent rice plants can come from the rice variety Roy J. Thus, any such methods using the rice variety Roy J are part of this invention: selfing, backcrosses, hybrid production, crosses to populations, and the like. All plants produced using rice variety Roy J as a parent are within the scope of this invention, including those developed from varieties derived from rice variety Roy J. Advantageously, the rice variety could be used in crosses with other, different, rice plants to produce the first generation ($F_1$) rice hybrid seeds and plants with superior characteristics. The variety of the invention can also be used for transformation where exogenous genes are introduced and expressed by the variety of the invention. Genetic variants created either through traditional breeding methods using variety Roy J or through transformation of Roy J by any of a number of protocols known to those of skill in the art are intended to be within the scope of this invention.

The following describes breeding methods that may be used with cultivar Roy J in the development of further rice plants. One such embodiment is a method for developing a Roy J progeny rice plant in a rice plant breeding program comprising: obtaining the rice plant, or a part thereof, of cultivar Roy J utilizing said plant or plant part as a source of breeding material and selecting a Roy J progeny plant with molecular markers in common with Roy J and/or with morphological and/or physiological characteristics selected from the characteristics listed in Tables 2 or 3. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar Roy J progeny rice plants, comprising crossing cultivar Roy J with another rice plant, thereby producing a population of rice plants, which, on average, derive 50% of their alleles from cultivar Roy J. A plant of this population may be selected and repeatedly selfed or sibbed with a rice cultivar resulting from these successive filial generations. One embodiment of this invention is the rice cultivar produced by this method and that has obtained at least 50% of its alleles from cultivar Roy J.

One of ordinary skill in the art of plant breeding would know how to evaluate the traits of two plant varieties to determine if there is no significant difference between the two traits expressed by those varieties. For example, see, Fehr and Walt, Principles of Cultivar Development, pp. 261-286 (1987). Thus the invention includes rice cultivar Roy J progeny rice plants comprising a combination of at least two Roy J traits selected from the group consisting of those listed in the Tables herein, or the Roy J combination of traits listed in the Summary of the Invention, so that said progeny rice plant is not significantly different for said traits than rice cultivar Roy J as determined at the 5% significance level when grown in the same environment. Using techniques described herein, molecular markers may be used to identify said progeny plant as a Roy J progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of rice cultivar Roy J may also be characterized through their filial relationship with rice cultivar Roy J, as for example, being within a certain number of breeding crosses of rice cultivar Roy J. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice cultivar Roy J and its progeny. For example, progeny produced by the methods described herein may be within 1, 2, 3, 4, or 5 breeding crosses of rice cultivar Roy J.

Pedigree Breeding

Pedigree breeding starts with the crossing of two genotypes, such as rice cultivar Roy J and another rice plant having one or more desirable characteristics that is lacking or which complements rice cultivar Roy J. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the nonrecurrent parent by stopping the backcrossing at an early stage and proceeding with selfing and selection. For example, a rice variety may be crossed with another rice variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new rice varieties.

Therefore, an embodiment of this invention is a method of making a backcross conversion of rice cultivar Roy J, comprising the steps of crossing a plant of rice cultivar Roy J with a donor plant comprising a desired trait, selecting an $F_1$ progeny plant comprising the desired trait, and backcrossing the selected $F_1$ progeny plant to a plant of rice cultivar Roy J. This method may further comprise the step of obtaining a molecular marker profile of rice cultivar Roy J and using the molecular marker profile to select for a progeny plant with the desired trait and the molecular marker profile of rice cultivar Roy J. In one embodiment the desired trait is a mutant gene or transgene present in the donor parent.

Recurrent Selection and Mass Selection

Recurrent selection is a method used in a plant breeding program to improve a population of plants. Rice cultivar Roy J is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the inter-crossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into rice cultivar Roy J. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development," Fehr, Macmillan Publishing Company (1983). In addition, mutations created in other rice plants may be used to produce a backcross conversion of rice cultivar Roy J that comprises such mutation.

Breeding with Molecular Markers

Molecular markers may be used in plant breeding methods utilizing rice cultivar Roy J.

Isozyme Electrophoresis and RFLPs have been widely used to determine genetic composition. See, for example, Dinka, S. J., et al., "Predicting the size of the progeny mapping population required to positionally clone a gene," *Genetics.*, 176(4):2035-54 (2007); Gonzalez, C., et al., "Molecular and pathogenic characterization of new *Xanthomonas oryzae* strains from West Africa," *Mol. Plant. Microbe Interact.*, 20(5):534-546 (2007); Jin, H., et al., "Molecular and cytogenic characterization of an *Oryza officinalis-O. sativa* chromosome 4 addition line and its progenies," *Plant Mol. Biol.*, 62(4-5):769-777 (2006); Pan, G., et al., "Map-based cloning of a novel rice cytochrome P450 gene CYP81A6 that confers resistance to two different classes of herbicides," *Plant Mol. Biol.*, 61(6):933-943 (2006); Huang, W., et al., "RFLP analysis for mitochondrial genome of CMS-rice," *Journal of Genetics and Genomics.*, 33(4):330-338 (2007); Yan, C. J., et al., "Identification and characterization of a major QTL responsible for erect panicle trait in japonica rice (*Oryza sativa* L.)," *Theor. Appl. Genetics., DOI:*10.1007/s00122-007-0635-9 (2007); and I. K. Vasil (ed.), *DNA-based markers in plants*, Kluwer Academic Press Dordrecht, the Netherlands.

SSR technology is currently the most efficient and practical marker technology; more marker loci can be routinely used and more alleles per marker locus can be found using SSRs in comparison to RFLPs. Gealy, David, et al., "Insights into the Parentage of Rice/red Rice Crosses Using SSR Analysis of US Rice Cultivars and Red Rice Populations," *Rice Technical Working Group Meeting Proceedings, Abstract,* p. 179; Lawson, Mark J., et al., "Distinct Patterns of SSR Distribution in the *Arabidopsis thaliana* and rice genomes," *Genome Biology,* 7:R14 (2006); Nagaraju, J., et al., "Genetic Analysis of Traditional and Evolved Basmati and Non-Basmati Rice Varieties by Using Fluorescence-based ISSR-PCR and SSR Markers," *Proc. Nat. Acad. Sci. USA.,* 99(9):5836-5841 (2002); and Lu, Hong, et al., "Population Structure and Breeding Patterns of 145 US Rice Cultivars Based on SSR Marker Analysis," *Crop Science,* 45:66-76 (2005). Single Nucleotide Polymorphisms may also be used to identify the unique genetic composition of the invention and progeny varieties retaining that unique genetic composition. Various molecular marker techniques may be used in combination to enhance overall resolution.

Rice DNA molecular marker linkage maps have been rapidly constructed and widely implemented in genetic studies such as in Zhu, J. H., et al., "Toward rice genome scanning by map-based AFLP fingerprinting," *Mol. Gene. Genetics.*, 261(1):184-195 (1999); Cheng, Z., et al., "Toward a cytological characterization of the rice genome," *Genome Research.,* 11(12):2133-2141 (2001); Ahn, S., et al., "Comparative linkage maps of the rice and maize genomes," *Proc. Natl. Acad. Sci. USA,* 90(17):7980-7984 (1993); and Kao, F. I., et al., "An integrated map of *Oryza sativa* L. chromosome 5," *Theor. Appl. Genet.,* 112(5):891-902 (2006). Sequences and PCR conditions of SSR Loci in rice as well as the most current genetic map may be found in RiceBLAST and the TIGR Rice Genome Annotation on the World Wide Web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a rice plant for which rice cultivar Roy J is a parent can be used to produce double haploid plants. Double haploids are produced by the doubling of a set of chromosomes (1N) from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics,* 77:889-892 (1989), and U.S. Pat. No. 7,135,615.

Methods for obtaining haploid plants are also disclosed in Kobayashi, M., et al., *Journ. of Heredity,* 71(1):9-14 (1980), Pollacsek, M., 12(3):247-251, Agronomie, Paris (1992); Cho-Un-Haing, et al., *Journ. of Plant Biol.,* 39(3):185-188 (1996); Verdoodt, L., et al., 96(2):294-300 (February 1998); Genetic Manipulation in Plant Breeding, Proceedings International Symposium Organized by EUCARPIA, Berlin, Germany (Sep. 8-13, 1985); Thomas, W J K, et al., "Doubled haploids in breeding," in Doubled Haploid Production in Crop Plants, Maluszynski, M., et al. (Eds.), Dordrecht, The Netherland Kluwer Academic Publishers, pp. 337-349 (2003).

Descriptions of other breeding methods that are commonly used for different traits and crops can be found in one of several reference books (e.g., Allard (1960); Simmonds (1979); Sneep, et al. (1979); Fehr (1987)).

The seed of rice cultivar Roy J, the plant produced from the cultivar seed, the hybrid rice plant produced from the crossing of the cultivar, hybrid seed, and various parts of the hybrid rice plant and transgenic versions of the foregoing, can be utilized for human food, livestock feed, and as a raw material in industry.

Tables

In Table 2, agronomic characteristics are shown for rice cultivar Roy J and for eight other rice cultivars. These data are the result of the ARPT conducted in 2007. (Stuttgart, Rice Research and Extension Center (RREC); Keiser, Northeast Research and Extension Center (NEREC); Rohwer, Southeast Research and Extension Center (SEREC-RD); Clay Co. and Jackson Co.). Column one shows the variety, column two shows the yield in bushels per acre, column three shows the plant height in inches, column four shows the maturity in days at 50% heading, column five shows the kernel weight in milligrams and column six shows the milling percent head rice (or whole kernel rice) as compared to the percent of total milled rice. Milling data collected from RREC, NEREC, Clay Co., and Jackson Co. test plots.

TABLE 2

| Variety | Yield (BU/AC) | Height (IN.) | Maturity (50% HD) | Kernel weight (mg) | Milling HR:TOT |
|---|---|---|---|---|---|
| Roy J | 215 | 42 | 93 | 18.3 | 54:70 |
| Taggart | 190 | 44 | 92 | 19.6 | 50:71 |
| Templeton | 179 | 40 | 90 | 16.0 | 51:70 |
| Francis | 185 | 38 | 87 | 17.2 | 53:70 |
| Wells | 185 | 41 | 88 | 18.7 | 48:70 |
| LaGrue | 186 | 44 | 90 | 17.5 | 52:69 |
| Cybonnet | 171 | 35 | 89 | 17.8 | 58:71 |
| Cocodrie | 163 | 36 | 88 | 17.9 | 61:70 |
| Drew | 175 | 43 | 91 | 16.0 | 53:69 |

In Table 3, agronomic characteristics are shown for rice cultivar Roy J and for eight other rice cultivars. These data are the result of the ARPT conducted in 2008 (Stuttgart, RREC; Keiser, NEREC; Colt, PTS; Clay Co. and Jackson Co.). Column one shows the variety, column two shows the yield in bushels per acre, column three shows the plant height in inches, column four shows the maturity in days at 50% heading, column five shows the kernel weight in milligrams and column six shows the milling percent head rice (or whole kernel rice) as compared to the percent of total milled rice. Milling data collected from RREC, NEREC, and Jackson Co. test plots.

TABLE 3

| Variety | Yield (BU/AC) | Height (IN.) | Maturity (50% HD) | Kernel weight (mg) | Milling HR:TOT |
|---|---|---|---|---|---|
| Roy J | 186 | 42 | 95 | 18.3 | 61:71 |
| Taggart | 149 | 44 | 97 | 20.8 | 60:72 |
| Templeton | 144 | 41 | 93 | 16.3 | 57:71 |
| Francis | 152 | 39 | 90 | 17.4 | 62:72 |
| Wells | 157 | 40 | 92 | 19.0 | 56:72 |
| LaGrue | 144 | 44 | 93 | 18.0 | 56:70 |
| Cybonnet | 158 | 37 | 91 | 17.6 | 63:72 |
| Cocodrie | 144 | 36 | 88 | 17.7 | 63:72 |
| Drew | 136 | 43 | 94 | 15.8 | 60:71 |

In Table 4, agronomic characteristics are shown for rice cultivar Roy J and eight other rice cultivars. These data are the result of trials at the ARPT conducted in 2009 (Stuttgart, RREC; Keiser, NEREC; Colt, PTS; Clay Co. and Jackson Co.). Column one shows the variety; column two gives the yield for each variety in bushels per acre; column three shows the height in inches for the varieties; column four shows the maturity at 50% heading in days, and column five gives the milling percent head rice (or whole kernel rice) as compared to the percent of total milled rice. Milling data collected from RREC, PTES, SEREC, and Cross Co. test plots.

TABLE 4

| Variety | Yield (BU/AC) | Height (IN.) | Maturity (50% HD) | Milling HR:TOT |
|---|---|---|---|---|
| Roy J | 187 | 44 | 99 | 62:72 |
| Taggart | 184 | 45 | 96 | 65:73 |
| Templeton | 166 | 41 | 96 | 65:72 |
| Francis | 181 | 40 | 90 | 67:72 |
| Wells | 180 | 41 | 94 | 62:74 |
| LaGrue | 167 | 45 | 95 | 63:71 |
| Cybonnet | 155 | 37 | 93 | 68:73 |
| Cocodrie | 139 | 36 | 92 | 67:72 |
| Drew | 165 | 46 | 96 | 63:73 |

In Table 5, agronomic characteristics are shown for rice cultivar Roy J and eight other rice cultivars. These data are averages of the trials at the ARPT from 2007 to 2009. Column one shows the variety; column two gives the yield for each variety in bushels per acre; column three shows the height in inches for the varieties; column four shows the maturity at 50% heading in days; column five gives the milled kernel weight in milligrams, and column six gives the milling percent head rice (or whole kernel rice) as compared to the percent of total milled rice. Kernel weight data collected in 2007 and 2008.

TABLE 5

| Variety | Yield (BU/AC) | Height (IN.) | Maturity (50% HD) | Kernel weight (mg) | Milling HR:TOT |
|---|---|---|---|---|---|
| Roy J | 196 | 43 | 96 | 18.3 | 59:71 |
| Taggart | 174 | 44 | 95 | 20.2 | 58:72 |
| Templeton | 163 | 41 | 93 | 16.2 | 58:71 |
| Francis | 173 | 39 | 89 | 17.3 | 61:71 |
| Wells | 174 | 41 | 91 | 18.9 | 55:72 |
| LaGrue | 166 | 44 | 93 | 17.8 | 57:70 |
| Cybonnet | 161 | 36 | 91 | 17.7 | 64:72 |
| Cocodrie | 149 | 36 | 89 | 17.8 | 64:71 |
| Drew | 159 | 44 | 94 | 15.9 | 59:71 |

In Table 6, agronomic characteristics are shown for rice cultivar Roy J and eight other rice cultivars. The data are the result of trials at the ARPT from 2007. Column one shows the variety, columns two to six give the average grain yield for each of 5 different locations for each variety in bushels per acre, column seven gives the average grain yield for the 5 locations, columns eight to eleven show the average head rice (%) to total rice (%) ratio for each of 4 different locations and column twelve shows the average head rice (%) to total rice (%) ratio for the 4 locations. 2007 consisted of five locations: Rice Research and Extension Center (RREC), Stuttgart; Northeast Research and Extension Center (NEREC), Keiser, Ark.; Southeast Research and Extension Center Rohwer Division (SEREC-RD), Rohwer, Ark.; CL CO, and Jackson County producer field (JC). Milling figures are head rice:total milled rice.

TABLE 6

| VARIETY | GRAIN YIELD (BU/AC) | | | | | | HEAD RICE(%):TOTAL RICE(%) | | | | |
|---|---|---|---|---|---|---|---|---|---|---|---|
| | RREC | NEREC | SEREC | CL CO | JC | AVG | RREC | NEREC | CL CO | JC | AVG |
| Roy J | 182 | 226 | 195 | 232 | 239 | 215 | 52:71 | 53:69 | 57:68 | 55:71 | 54:70 |
| Taggart | 187 | 149 | 144 | 215 | 255 | 190 | 57:72 | 47:69 | 48:71 | 50:70 | 50:70 |
| Templeton | 163 | 128 | 158 | 207 | 237 | 179 | 57:71 | 48:67 | 55:70 | 45:71 | 51:70 |
| Francis | 199 | 93 | 163 | 218 | 249 | 185 | 62:72 | 43:68 | 57:71 | 55:71 | 53:70 |
| Wells | 172 | 168 | 150 | 203 | 230 | 185 | 54:72 | 33:66 | 53:72 | 52:72 | 48:70 |
| LaGrue | 162 | 140 | 181 | 203 | 242 | 186 | 56:70 | 47:66 | 52:69 | 55:70 | 52:69 |
| Cybonnet | 163 | 190 | 103 | 190 | 207 | 171 | 63:72 | 51:68 | 61:71 | 60:72 | 58:71 |
| Cocodrie | 176 | 144 | 95 | 162 | 238 | 163 | 62:72 | 58:69 | 62:70 | 63:71 | 61:70 |
| Drew | 167 | 153 | 148 | 191 | 216 | 175 | 51:69 | 49:67 | 59:70 | 50:71 | 53:69 |

In Table 7, agronomic characteristics are shown for the present invention, Roy J and eight other rice cultivars. The data are the result of trials at the ARPT from 2008. Column one shows the variety, columns two to seven give the average grain yield for each of 6 different locations for each variety in bushels per acre, column eight shows the average grain yield for the 6 locations, columns nine to eleven show the average head rice (%) to total rice (%) ratio for each of 3 different locations and column twelve shows the average head rice (%) to total rice (%) ratio for the 3 locations. 2008 consisted of six locations: RREC, Stuttgart, Ark.; NEREC, Keiser, Ark.; PTES, Colt, Ark.; SEREC, Rohwer, Ark.; Clay County, Ark.; and Jackson County (JC), Ark.

TABLE 7

| VARIETY | GRAIN YIELD (BU/AC) | | | | | | | HEAD RICE(%):TOTAL RICE(%) | | | |
|---|---|---|---|---|---|---|---|---|---|---|---|
| | RREC | NEREC | PTES | SEREC | CL CO | JC | AVG | RREC | NEREC | JC | AVG |
| Roy J | 190 | 169 | 186 | 160 | 255 | 154 | 186 | 67:73 | 62:71 | 56:71 | 61:71 |
| Taggart | 194 | 145 | 181 | 125 | 67 | 181 | 149 | 61:69 | 60:72 | 60:73 | 60:72 |
| Templeton | 184 | 181 | 156 | 130 | 83 | 127 | 144 | 64:71 | 59:71 | 49:69 | 57:71 |
| Francis | 196 | 187 | 167 | 138 | 62 | 163 | 152 | 63:70 | 59:71 | 64:74 | 62:72 |
| Wells | 194 | 172 | 177 | 151 | 115 | 133 | 157 | 66:74 | 60:72 | 45:71 | 56:72 |
| LaGrue | 171 | 158 | 162 | 167 | 57 | 147 | 144 | 65:71 | 54:69 | 51:69 | 56:70 |
| Cybonnet | 173 | 177 | 136 | 116 | 224 | 120 | 158 | 68:73 | 65:71 | 59:74 | 63:72 |
| Cocodrie | 158 | 173 | 150 | 117 | 124 | 144 | 144 | 66:71 | 67:74 | 58:72 | 63:72 |
| Drew | 162 | 146 | 161 | 97 | 125 | 129 | 136 | 67:73 | 58:70 | 57:71 | 60:71 |

In Table 8, agronomic characteristics are shown for rice cultivar Roy J, and eight other rice cultivars. The data are the result of an average of the trials at the ARPT conducted in 2009. Column one shows the variety, columns two to six give the average grain yield for each of 5 different locations for each variety in bushels per acre, column seven shows the average grain yield for the 5 locations, columns eight to eleven show the average head rice (%) to total rice (%) ratio for each of 4 different locations and column twelve shows the average head rice (%) to total rice (%) ratio for the 4 locations. 2009 consisted of five locations: RREC, Stuttgart, Ark.; NEREC, Keiser, Ark.; PTES, Colt, Ark.; SEREC, Rohwer, Ark.; and Cross County, Ark.

TABLE 8

| VARIETY | GRAIN YIELD (BU/AC) | | | | | | HEAD RICE(%):TOTAL RICE(%) | | | | |
|---|---|---|---|---|---|---|---|---|---|---|---|
| | RREC | NEREC | PTES | SEREC | CR CO | AVG | RREC | PTES | SEREC | CR CO | AVG |
| Roy J | 187 | 200 | 159 | 188 | 199 | 187 | 67:72 | 59:72 | 59:70 | 64:73 | 62:72 |
| Taggart | 183 | 176 | 159 | 193 | 203 | 183 | 67:72 | 60:73 | 63:71 | 71:75 | 65:73 |
| Templeton | 182 | 186 | 142 | 158 | 184 | 170 | 67:71 | 61:73 | 61:71 | 69:73 | 65:72 |
| Francis | 182 | 191 | 156 | 183 | 206 | 183 | 68:71 | 65:74 | 66:72 | 69:72 | 67:72 |
| Wells | 192 | 198 | 163 | 155 | 209 | 183 | 68:73 | 64:75 | 63:74 | 51:75 | 62:74 |
| LaGrue | 157 | 156 | 153 | 165 | 194 | 165 | 65:69 | 62:72 | 64:72 | 61:72 | 63:71 |
| Cybonnet | 161 | 166 | 139 | 123 | 199 | 157 | 69:72 | 69:76 | 66:73 | 66:73 | 68:73 |
| Cocodrie | 171 | 180 | 138 | 73 | 175 | 147 | 67:71 | 67:75 | 62:70 | 69:72 | 67:72 |
| Drew | 165 | 161 | 157 | 152 | 185 | 164 | 70:73 | 60:74 | 64:71 | 60:73 | 63:73 |
| C.V._05 | 5.8 | 8.0 | 8.2 | 11.0 | 11.0 | | | | | | |

In Table 9, agronomic characteristics are shown for rice cultivar Roy J and 8 other rice cultivars. The data are averages of trials from the ARPT conducted from 2007 to 2009. Column one shows the variety, columns two to eight show the grain yield in bushels per acre for 7 locations, and column nine shows the average grain yield for the 7 locations. Grain Yield data collected from RREC in 2007, 2008, 2009; NEREC in 2007, 2008, 2009; PTES in 2008, 2009; SEREC in 2007, 2008, 2009; Clay County in 2007, 2008; Cross County in 2009; and Jackson County in 2007, 2008.

TABLE 9

| VARIETY | GRAIN YIELD (BU/AC) | | | | | | | |
|---|---|---|---|---|---|---|---|---|
| | RREC | NEREC | PTES | SEREC | Clay Co. | Cross Co. | Jackson Co. | AVG |
| Roy J | 186 | 198 | 173 | 181 | 244 | 199 | 197 | 196 |
| Taggart | 188 | 157 | 170 | 154 | 141 | 203 | 218 | 172 |
| Templeton | 176 | 165 | 149 | 149 | 145 | 184 | 182 | 163 |
| Francis | 192 | 157 | 162 | 161 | 140 | 206 | 206 | 172 |
| Wells | 186 | 179 | 170 | 152 | 159 | 209 | 182 | 174 |
| LaGrue | 163 | 151 | 158 | 171 | 130 | 194 | 195 | 163 |
| Cybonnet | 166 | 178 | 138 | 114 | 207 | 199 | 164 | 162 |
| Cocodrie | 168 | 166 | 144 | 95 | 143 | 175 | 191 | 151 |
| Drew | 165 | 153 | 159 | 132 | 158 | 185 | 173 | 157 |

In Table 10, agronomic characteristics are shown for rice cultivar Roy J and 8 other rice cultivars. The data are averages of trials from the ARPT conducted from 2007 to 2009. Column one shows the variety, columns two to eight show the head rice (%) to total rice (%) ratio for 7 locations, and column nine shows the average head rice (%) to total rice (%) ratio for the 7 locations. Milling data collected from RREC in 2007, 2008, 2009; NEREC in 2007, 2008; PTES in 2009; SEREC in 2009; Clay County in 2007; Cross County in 2009; and Jackson County in 2007, 2008.

TABLE 10

| VARIETY | HEAD RICE(%):TOTAL RICE(%) | | | | | | | |
|---|---|---|---|---|---|---|---|---|
| | RREC | NEREC | PTES | SEREC | Clay Co. | Cross Co. | Jackson Co. | AVG |
| Roy J | 62:72 | 58:70 | 59:72 | 59:70 | 57:68 | 64:73 | 56:71 | 59:71 |
| Taggart | 62:71 | 54:71 | 60:73 | 63:71 | 48:71 | 71:75 | 55:72 | 59:72 |
| Templeton | 63:71 | 54:69 | 61:73 | 61:71 | 55:70 | 69:73 | 47:70 | 58:71 |
| Francis | 64:71 | 51:70 | 65:74 | 66:72 | 57:71 | 69:72 | 60:73 | 61:71 |
| Wells | 63:73 | 47:69 | 64:75 | 63:74 | 53:72 | 51:75 | 49:72 | 55:72 |
| LaGrue | 62:70 | 51:68 | 62:72 | 64:72 | 52:69 | 61:72 | 53:70 | 57:70 |
| Cybonnet | 67:72 | 58:70 | 69:76 | 66:73 | 61:71 | 66:73 | 60:73 | 64:72 |
| Cocodrie | 65:71 | 63:72 | 67:75 | 62:70 | 62:70 | 69:72 | 61:72 | 64:72 |
| Drew | 63:72 | 54:69 | 60:74 | 64:71 | 59:70 | 60:73 | 54:71 | 59:71 |

In Table 11, agronomic characteristics are shown for rice cultivar Roy J and 6 other rice cultivars. The data are the results from the Arkansas Uniform Regional Rice Nursery (URRN) conducted in 2008. Column one shows the variety, column two shows the grain yield in bushels per acre, column three shows the height in inches, column four shows the maturity in number of days from emergence to 50% heading, column five shows the kernel weight in milligrams, column six gives the milling percent head rice (or whole kernel rice) as compared to the percent of total milled rice.

TABLE 11

| VARIETY | YIELD (BU/AC) | HEIGHT (IN.) | MATURITY (50% HD) | KERNEL WT (MG) | MILLING HR:TOT |
|---|---|---|---|---|---|
| Roy J | 163 | 41 | 98 | 2.03 | 57:70 |
| Taggart | 185 | 41 | 95 | 2.20 | 58:70 |
| Templeton | 187 | 36 | 94 | 1.80 | 59:70 |
| Francis | 177 | 39 | 90 | 1.80 | 61:70 |
| Wells | 174 | 37 | 93 | 2.11 | 54:68 |
| Cybonnet | 160 | 35 | 93 | 1.84 | 65:71 |
| Cocodrie | 163 | 34 | 89 | 1.87 | 56:68 |

In Table 12, agronomic characteristics are shown for rice cultivar Roy J and 6 other rice cultivars. The data are the results from the Arkansas URRN conducted in 2009. Column one shows the variety, column two shows the grain yield in bushels per acre, column three shows the height in inches, column four shows the maturity in number of days from emergence to 50% heading, column five shows the kernel weight in milligrams, column six gives the milling percent head rice (or whole kernel rice) as compared to the percent of total milled rice.

TABLE 12

| VARIETY | YIELD (BU/AC) | HEIGHT (IN.) | MATURITY (50% HD) | KERNEL WT (MG) | MILLING HR:TOT |
|---|---|---|---|---|---|
| Roy J | 192 | 40 | 100 | 1.92 | 60:72 |
| Taggart | 191 | 43 | 94 | 2.20 | 58:71 |
| Templeton | 158 | 38 | 96 | 1.73 | 55:71 |
| Francis | 149 | 36 | 92 | 1.78 | 56:71 |
| Wells | 159 | 38 | 94 | 2.03 | 58:73 |
| Cybonnet | 158 | 36 | 95 | 1.83 | 61:72 |
| Cocodrie | 148 | 36 | 93 | 1.97 | 66:73 |

In Table 13, agronomic characteristics are shown for rice cultivar Roy J and 6 other rice cultivars. The data are averages of results from the Arkansas URRN from 2008 to 2009. Column one shows the variety, column two shows the grain yield in bushels per acre, column three shows the height in inches, column four shows the maturity in number of days from emergence to 50% heading, column five shows the kernel weight in milligrams, column six gives the milling percent head rice (or whole kernel rice) as compared to the percent of total milled rice.

TABLE 13

| VARIETY | YIELD (BU/AC) | HEIGHT (IN.) | MATURITY (50% HD) | KERNEL WT (MG) | MILLING HR:TOT |
|---|---|---|---|---|---|
| Roy J | 178 | 41 | 99 | 1.98 | 59:71 |
| Taggart | 188 | 43 | 95 | 2.20 | 58:71 |
| Templeton | 173 | 37 | 95 | 1.77 | 57:71 |
| Francis | 163 | 38 | 91 | 1.79 | 59:71 |
| Wells | 167 | 38 | 94 | 2.07 | 56:71 |
| Cybonnet | 159 | 36 | 94 | 1.84 | 63:72 |
| Cocodrie | 156 | 35 | 91 | 1.92 | 61:71 |

In Table 14, agronomic characteristics are shown for rice cultivar Roy J and 6 other rice cultivars. The data are the result of trials at the Arkansas URRN from 2008. Column one shows the variety, columns two to six give the average grain yield for each of 5 different locations for each variety in bushels per acre, column seven shows the average grain yield for the 5 locations, columns eight to eleven show the average head rice (%) to total rice (%) ratio for each of four different locations and column twelve shows the average head rice (%) to total rice (%) ratio for the four locations.

TABLE 14

| | GRAIN YIELD (BU/AC) | | | | | | HEAD RICE(%):TOTAL RICE(%) | | | | |
|---|---|---|---|---|---|---|---|---|---|---|---|
| VARIETY | AR | LA | MO | MS | TX | AVG | AR | LA | MS | TX | AVG |
| Roy J | 164 | 237 | 202 | 211 | 257 | 214 | 57:70 | 57:70 | 52:68 | 61:74 | 55:71 |
| Taggart | 185 | 244 | 184 | 214 | 253 | 216 | 58:70 | 57:70 | 48:68 | 53:73 | 54:70 |
| Templeton | 187 | 185 | 147 | 184 | 226 | 186 | 59:70 | 61:69 | 53:68 | 66:73 | 60:71 |
| Francis | 177 | 228 | 167 | 222 | 200 | 191 | 61:70 | 59:68 | 45:65 | 56:72 | 55:69 |
| Wells | 174 | 248 | 148 | 197 | 234 | 200 | 54:68 | 57:68 | 51:69 | 60:73 | 55:70 |
| Cybonnet | 160 | 205 | 181 | 178 | 223 | 189 | 65:71 | 66:72 | 54:67 | 66:73 | 63:72 |
| Cocodrie | 163 | 216 | 159 | 209 | 225 | 194 | 56:68 | 62:70 | 54:68 | 63:74 | 59:70 |

In Table 15, agronomic characteristics are shown for rice cultivar Roy J and 6 other rice cultivars. The data are the result of trials at the Arkansas URRN from 2009. Column one shows the variety, columns two to six give the average grain yield for each of 5 different locations for each variety in bushels per acre, column seven shows the average grain yield for the 5 locations, columns eight to twelve show the average head rice (%) to total rice (%) ratio for each of four different locations and column thirteen shows the average head rice (%) to total rice (%) ratio for the four locations.

TABLE 15

| | GRAIN YIELD (BU/AC) | | | | | | HEAD RICE(%):TOTAL RICE(%) | | | | | |
|---|---|---|---|---|---|---|---|---|---|---|---|---|
| VARIETY | AR | LA | MO | MS | TX | AVG | AR | LA | MO | MS | TX | AVG |
| Roy J | 192 | 201 | 207 | 198 | 204 | 200 | 60:72 | 57:71 | 57:74 | 65:73 | 54:74 | 59:73 |
| Taggart | 191 | 214 | 206 | 209 | 239 | 212 | 58:71 | 58:72 | 58:75 | 65:72 | 55:72 | 59:72 |
| Templeton | 158 | 201 | 183 | 193 | 210 | 189 | 55:71 | 66:71 | 59:74 | 72:75 | 64:73 | 64:73 |
| Francis | 149 | 204 | 185 | 206 | 211 | 188 | 56:71 | 57:71 | 62:75 | 69:72 | 64:73 | 61:72 |
| Wells | 159 | 200 | 204 | 190 | 203 | 191 | 58:73 | 56:71 | 58:75 | 70:75 | 63:75 | 61:74 |
| Cybonnet | 158 | 185 | 218 | 171 | 198 | 186 | 61:72 | 65:72 | 68:75 | 71:75 | 66:74 | 66:74 |
| Cocodrie | 148 | 203 | 205 | 194 | 208 | 191 | 66:73 | 65:72 | 63:75 | 71:76 | 64:74 | 67:74 |

In Table 16, agronomic characteristics are shown for rice cultivar Roy J and 6 other rice cultivars. The data are averages of trials at the Arkansas URRN from 2008 to 2009. Column one shows the variety, columns two to six give the average grain yield for each of 5 different locations for each variety in bushels per acre, column seven shows the average grain yield for the 5 locations, columns eight to twelve show the average head rice (%) to total rice (%) ratio for each of four different locations and column thirteen shows the average head rice (%) to total rice (%) ratio for the four locations. Missouri milling data for 2009 only.

TABLE 16

| | GRAIN YIELD (BU/AC) | | | | | | HEAD RICE(%):TOTAL RICE(%) | | | | | |
|---|---|---|---|---|---|---|---|---|---|---|---|---|
| VARIETY | AR | LA | MO | MS | TX | AVG | AR | LA | MO* | MS | TX | AVG |
| Roy J | 178 | 219 | 205 | 205 | 231 | 207 | 59:71 | 57:71 | 57:74 | 59:72 | 58:74 | 58:72 |
| Taggart | 188 | 229 | 195 | 212 | 246 | 214 | 58:71 | 58:71 | 58:75 | 57:70 | 54:73 | 57:72 |
| Templeton | 173 | 193 | 165 | 189 | 218 | 188 | 57:71 | 64:70 | 59:74 | 63:72 | 65:73 | 62:72 |
| Francis | 163 | 216 | 176 | 214 | 206 | 190 | 59:71 | 58:70 | 62:75 | 57:69 | 60:73 | 59:71 |
| Wells | 167 | 224 | 176 | 194 | 219 | 196 | 56:72 | 57:70 | 58:75 | 61:72 | 62:74 | 59:72 |
| Cybonnet | 159 | 195 | 200 | 175 | 211 | 188 | 63:72 | 66:72 | 68:75 | 63:71 | 66:74 | 65:73 |
| Cocodrie | 156 | 210 | 182 | 202 | 217 | 193 | 61:71 | 64:71 | 63:75 | 63:71 | 64:74 | 63:72 |

Table 17 shows kernel characteristics for rice cultivars Roy J, Taggart, and Templeton. The data are averages of the following trials, 2007 ARPT RREC, 2007 Breeder Head Row Seed RREC, 2007 Stuttgart Initial Test Group 5 and 2008 Stuttgart, Initial Test Groups 4, 5 and 6. Column 1 shows the variety, column 2 shows the class, column 3 shows the length in millimeters, column 4 shows the width in millimeters, column 5 shows the thickness in millimeters, and column 6 shows the length to width ratio and column 7 shows the kernel weight in milligrams.

TABLE 17

| Variety | Class | Length | Width | Thickness | L/W | Kernel Weight |
|---|---|---|---|---|---|---|
| Roy J | Rough | 9.50 | 2.38 | 1.93 | 3.99 | 22.9 |
| Taggart | Rough | 9.62 | 2.58 | 2.05 | 3.73 | 25.9 |
| Templeton | Rough | 9.24 | 2.36 | 1.95 | 3.92 | 21.8 |
| Roy J | Brown | 7.33 | 2.13 | 1.78 | 3.44 | 19.7 |
| Taggart | Brown | 7.59 | 2.29 | 1.79 | 3.31 | 21.2 |
| Templeton | Brown | 7.16 | 2.11 | 1.73 | 3.40 | 17.7 |
| Roy J | Milled | 6.81 | 2.09 | 1.71 | 3.26 | 18.5 |
| Taggart | Milled | 7.22 | 2.28 | 1.74 | 3.17 | 19.7 |
| Templeton | Milled | 6.65 | 2.10 | 1.67 | 3.17 | 16.2 |

Disease Evaluations for Rice Cultivar Roy J
Greenhouse Blast Tests

Rice diseases are usually rated visually on a 0-9 scale to estimate degree of severity. Numerical data is often converted to this scale. A rating of zero indicates complete disease immunity. A rating of one to three indicates resistance where little loss occurs and in the case of rice blast pathogen growth is restricted considerably. Conversely, a nine rating indicates maximum disease susceptibility, which typically results in complete plant death and/or yield loss. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible) 7=S (susceptible) and 8-9 VS (very susceptible). Exceptions to established ratings do occur unexpectedly as disease situations change.

Greenhouse blast tests are the primary means of screening large number of entries for varietal reaction to the many blast races occurring in the production areas. Although results are quite variable and testing conditions tends to overwhelm any field resistance present in the entry, this test provides an accurate definition of the fungus-variety genetics. Blast field nurseries, utilizing both natural and lab produced inoculum, are established in an effort to better define blast susceptibility under field conditions. Since field nursery is also quite variable, new techniques are currently being developed and evaluated to better estimate cultivar field resistance to blast.

Tables 18 summarizes available leaf blast rating data (a) from Roy J and seven comparison plants inoculated with the indicated race using standard greenhouse techniques. (b) Data were taken from 2008 to 2009. Column one shows the variety and columns 2 to 17 show leaf blast rating data of each race for each variety.

TABLE 18

| VARIETY | IB-1 | IB-1 | IB-49 | IB-49 | IC-17 | IC-17 | IE-1 | IE-1 | IG-1 | IG-1 | IH-1 | IH-1 | IE-1K | IE-1K | IB-33 | IB-33 |
|---|---|---|---|---|---|---|---|---|---|---|---|---|---|---|---|---|
| Roy J | 6 | S | 6 | S | 1 | MR | 5 | S | 6 | S | 7 | S | 5 | S | 7 | S |
| Templeton | 1 | R | 0 | R | 0 | R | 0 | R | 0 | R | 0 | R | 2* | MS | 7 | S |
| Taggart | 5 | S | 5 | S | 6 | S | 6 | S | 7 | S | 6 | S | 4** | MS | 7 | S |
| Banks | 2 | R | 1 | R | 0 | R | 0 | R | 1 | R | 1 | R | 7 | S | 8 | S |
| Cybonnet | 1 | R | 0 | R | 0 | R | 0 | R | 0 | R | 0 | R | 6 | S | 6 | S |
| Drew | 1 | R | 0 | R | 0 | R | 0 | R | 0 | R | 0 | R | 6 | S | 6 | S |
| Francis | 6 | S | 7 | S | 8 | S | 6 | S | 7 | S | 1 | S | 6 | S | 7 | S |
| Wells | 7 | S | 7 | S | 7 | S | 7 | S | 2 | S | 0 | S | 6 | S | 7 | S | a) Standard visual rating scale 0-9 where 0 = resistant and 9 = very susceptible.
b) Plants in the 3-r leaf growth stage were sprayed with spore suspension, held in moist chamber 12-18 hours then moved to greenhouse conditions.
*Mean value of variable data presented. Ratings from seven tests were less than zero (R). However, mean ratings from four additional tests was 4.5 (S). Entry may likely to be susceptible to this race in moisture stress conditions.
**Mean value of variable data presented. Ratings from four tests were less than two (R). However, mean ratings from one additional tests was 6 (S). Data are insufficient to accurately indicate susceptibility to this race.

Field Nursery Tests

Field nurseries are established and artificially inoculated to provide a uniform disease pressure for evaluations under field conditions. Established grower nurseries operate in an effort to evaluate disease reactions in grower fields under current production practices. Over time these nurseries document variety performance under adverse disease conditions in Arkansas production fields.

Table 19 is a summary of available blast rating data (a) from upland field blast nurseries inoculated using standard techniques (b) for Roy J and six comparison varieties. Data were taken from 2007 to 2009. Column 1 shows the variety name, columns 2 to 3 show the PTES Panicle Blast Rating and columns 4 to 5 show the PTES Leaf Blast Rating.

Table 20 is a summary of available Sheath Blight rating data (a) for Roy J and seven comparison varieties from field nurseries inoculated using standard techniques. (b) Data were taken from 2007 to 2009. Column 1 shows the variety, column 2 shows the mean overall numerical rating, column 3 shows the range of ratings, and column 4 shows the overall rating.

TABLE 19

| VARIETY | PTES PANICLE BLAST RATING | PTES PANICLE BLAST RATING | PTES LEAF BLAST RATING | PTES LEAF BLAST RATING |
|---|---|---|---|---|
| Roy J | 5.2 | S | 2.9 | S |
| Templeton | 2 | R | 0.9 | R |
| Taggart | 4 | S-MS | 3.7 | S |
| Banks | 3.7 | R | 0.5 | R |
| Cybonnet | 2.7 | R | 1.3 | R |
| Francis | 7.5 | S | 6 | S |
| Wells | 6.1 | S | 5.6 | S | a) Standard visual rating scale 0-9 where 0=resistant (S) and 9=very susceptible (VS). Leaf blast ratings were made on plants soon after inoculation. Panicle blast ratings were made at or near grain fill.
b) Upland nursery plants in 4-6 leaf growth stage were artificially inoculated with multiple races IB-1, IB-49, IC-17, IE-1, 1H-1 and IG-1 growing on rye grass seed. Plots were flooded as necessary with plants being drought stressed during the growing season, particularly after panicle exsertion.

TABLE 20

| VARIETY | MEAN OVERALL NUMERICAL RATING | RANGE OF RATINGS | OVERALL RATING |
|---|---|---|---|
| Roy J | 5.8 | 5-6 | S |
| Templeton | 5.8 | 5-7 | S |
| Taggart | 5.5 | 4-7 | S |
| Banks | 5.8 | 5-7 | S |
| Cybonnet | 7 | 6-8 | VS |
| Drew | 6.1 | 5-7 | S |
| Francis | 6.5 | 6-8 | S-VS |
| Wells | S | S | S | a) Standard visual rating scale 0-9 where 0=resistant (R) and 9=very susceptible (VS). Standard sheath blight ratings were made after grain fill as plants neared maturity.
b) Nursery plants growing under typical flood irrigation were artificially inoculated at or near beginning internode elongation with the pathogen growing on corn and rye grass seed.

Table 21 compares Roy J and 9 other rice cultivars for yield in bushels per acre and the amount of false smut galls per pound of grain when each variety is left untreated or treated with QUADKIS fungicide. Data were taken in September of 2009 in Arkansas.

TABLE 21

| VARIETY | TREATMENT | YIELD BU/A | FALSE SMUT galls/lb |
|---|---|---|---|
| Roy J | Untreated | 204 | 5.8 |
| Roy J | QUADRIS 12 fl oz/A | 215 | 4.3 |
| Wells | Untreated | 193 | 0.0 |
| Wells | QUADRIS 12 fl oz/A | 201 | 0.7 |
| Neptune | Untreated | 206 | 0.0 |
| Neptune | QUADRIS 12 fl oz/A | 214 | 0.3 |
| CFX 111 | Untreated | 148 | 0.2 |
| CFX 111 | QUADRIS 12 fl oz/A | 174 | 0.6 |
| Taggart | Untreated | 203 | 2.5 |
| Taggart | QUADRIS 12 fl oz/A | 214 | 5.0 |
| Templeton | Untreated | 187 | 3.6 |
| Templeton | QUADRIS 12 fl oz/A | 201 | 4.2 |
| CL 151 | Untreated | 181 | 1.3 |
| CL 151 | QUADRIS 12 fl oz/A | 203 | 2.0 |
| Arize 1003 | Untreated | 171 | 4.5 |
| Arize 1003 | QUADRIS 12 fl oz/A | 218 | 4.3 |
| CL 181 | Untreated | 159 | 1.4 |
| CL 181 | QUADRIS 12 fl oz/A | 172 | 3.4 |
| CL 142 | Untreated | 174 | 0.4 |
| CL 142 | QUADRIS 12 fl oz/A | 182 | 0.0 |

Table 22 is a summary of rice variety reactions (1) to diseases from the ARPT fact sheet (2009). Column 1 shows the variety or hybrid name, column 2 shows the reaction to Sheath Blight, column 3 shows the reaction to Blast, column 4 shows the reaction to Straighthead, column 5 shows the reaction to Bacterial Panicle Blight, column 6 shows the reaction to Narrow Brown Leaf Spot, column 7 shows the reaction to Stem Rot, column 8 shows the reaction to Kernel Smut, column 9 shows the reaction to False Smut, column 10 shows the reaction to Brown Spot, column 11 shows the lodging score, and column 12 shows the reaction to Black Sheath Rot.

For Table 22, Reaction: R=Resistant; MR=Moderately Resistant; MS=Moderately Susceptible; S=Susceptible; VS=Very Susceptible. Reactions were assigned based on cultivar assessment data collected across multiple locations and years in Arkansas. In general, assessment data were collected using published 0-9 severity scales for the respective disease, and from sites where conditions favored uniform disease severity across varieties. Locations included on-farm rice disease monitoring program test sites, URRN test plots, ARPT test plots, grower fields, rice disease nurseries at the Rice Research and Extension Center near Stuttgart and the Pine Tree Branch Experiment Station near Colt and fungicide test plots in Arkansas; and the LSU Rice Station (Crowley, La.). Reactions above would be expected in commercial fields where conditions strongly favor development of one or more of the listed diseases.

Blast ratings were based on reaction to common races of the rice blast fungus in Arkansas. Race IE-1k of the blast pathogen is relatively rare in the state, but can attack all varieties with primary resistance conferred by the Pi-ta blast resistance gene (e.g. Banks). Because of the ability of the blast fungus to develop new races and overcome host resistance, all rice varieties (including hybrids) should be monitored annually for blast symptoms and suspect samples submitted to the Cooperative Extension Service Plant Health Clinic thru the local county extension office for testing and confirmation.

Most cultivars will be susceptible to stem rot under low K and high N conditions. Bengal and certain other cultivars become very susceptible to brown spot under low K conditions. Low soil K may also increase other diseases, including sheath blight, narrow brown leaf spot, etc. Most cultivars are susceptible to false smut under high N, late planted conditions. Kernel smut, false smut and many other diseases are increased by excessive nitrogen fertilization, especially when applied at preflood.

TABLE 22

| Variety/Hybrid | Sheath Blight | Blast | Straight-head | Bacterial Panicle Blight | Narrow Brown Leaf Spot | Stem Rot | Kernel Smut | False Smut | Brown Spot | Lodging | Black Sheath Rot |
|---|---|---|---|---|---|---|---|---|---|---|---|
| Roy J | MS | S | S | S | MR | S | S | S | R | MR | MS |
| Bengal | MS | S | VS | VS | S | VS | MS | MS | VS | MR | MR |
| Bowman | MS | VS | MR | S | MR | VS | MS | S | R | MR | MS |
| Catahoula | VS | R | MS | S | MR | S | S | S | R | MR | MS |
| Cheniere | S | S | MR | S | S | S | S | S | R | MR | S |
| CL 131 | VS | MS | VS | VS | VS | VS | S | S | R | MR | S |
| CL142-AR | MS | S | MS | S | S | S | S | S | R | MS | S |
| CL 151 | S | VS | VS | VS | S | VS | S | S | R | S | S |
| CL 161 | VS | S | MS | S | S | VS | S | S | R | MS | S |
| CL 171-AR | VS | S | MS | S | S | VS | S | S | R | MS | S |
| CL181-AR | VS | S | MS | VS | S | VS | S | S | R | MR | S |
| Cocodrie | S | S | VS | S | S | VS | S | S | R | MR | MS |
| Cybonnet | VS | R | R | S | S | VS | S | S | R | MS | S |
| Francis | MS | VS | MR | VS | S | S | VS | S | R | MS | MS |
| JES | MS | R | MR | MS | R | VS | MS | MS | R | S | MR |
| Jupiter | S | S | S | MR | MS | VS | MS | MS | R | MS | MR |
| Neptune | MS | MS | VS | S | MS | VS | MS | MS | R | MR | MR |
| RT CL XL 745 | MS | R | R | MR | MS | MS | MS | S | R | S | MS |
| RT CL XL729 | MS | R | MS | MR | MS | MS | MS | S | R | S | MS |
| RT XL723 | MS | R | S | MR | MS | MS | MS | S | R | MS | MS |
| Templeton | MS | R | S | S | S | MS | S | S | R | MS | MS |
| Taggart | MS | S | R | MS | MS | S | S | S | R | MS | MS |
| Wells | S | S | MS | S | S | VS | S | S | R | MS | MS |

Physiological Evaluations for Rice Cultivar Roy J

Straighthead

Straighthead is a physiological disorder which appears to be effected by the oxygen potential of the soil. Under certain conditions, arsenic levels can increase in these soils or on soils where cotton has been grown and MSMA or other arsenical pesticides have been applied. Straighthead may also occur in soils high in organic matter. Symptoms can only be detected after panicle emergence and fail to produce grain. Foliage tends to remain dark green. Rice grains may be distorted especially on long-grain varieties forming a parrot-beak on the end of the hull. Floral parts may also be missing and under severe conditions panicle fail to emerge from the boot.

In Table 23, the reaction of Roy J to Straighthead is compared to various rice cultivars in three separate trials from 2007 in ARPT, and 2008 to 2009 in URRN and ARPT, ratings based on standard scale. Column two shows the variety name, columns 3 to 5 show rep 1, rep 2 and rep 3, respectively, and column 6 shows the mean of reps 1 to 3.

TABLE 23

|  |  | Rep1 | Rep2 | Rep3 | Mean |
|---|---|---|---|---|---|
| 2007 Straighthead ARPT | Roy J | 7 | 6 | 7 | 6.7 |
|  | Templeton | 7 | 7 | 7 | 7.0 |
|  | Taggart | 6 | 4 | 5 | 5.0 |
|  | Cybonnet | 3 | 3 | 5 | 3.7 |
|  | Wells | 6 | 6 | 7 | 6.3 |

TABLE 23-continued

|  |  | Rep1 | Rep2 | Rep3 | Mean |
|---|---|---|---|---|---|
| 2008 Straighthead URRN | Roy J | 7 | 5 | 6 | 6.0 |
|  | Tempelton | 7 | 8 | 7 | 7.3 |
|  | Taggart | 7 | 5 | 7 | 6.3 |
|  | Cybonnet | 6 | 5 | 6 | 5.6 |
|  | Wells | 7 | 7 | 7 | 7.0 |
| 2008 Straighthead ARPT | Roy J | 6 | 6 | 7 | 6.3 |
|  | Templeton | 7 | 8 | 7 | 7.3 |
|  | Taggart | 5 | 5 | 5 | 5.0 |
|  | Cybonnet | 4 | 5 | 5 | 4.7 |
|  | Wells | 6 | 7 | 7 | 6.7 |
| 2009 Straighthead URRN | Roy J | 3 | 6 | 6 | 5.0 |
|  | Templeton | 7 | 8 | 8 | 7.7 |
|  | Taggart | 6 | 6 | — | 6.0 |
|  | Cybonnet | 3 | 2 | 2 | 2.7 |
|  | Wells | 6 | 7 | 7 | 6.7 |
| 2009 Straighthead ARPT | Roy J | 6 | 7 | 7 | 6.7 |
|  | Templeton | 7 | 8 | 7 | 7.7 |
|  | Taggart | 6 | 6 | 7 | 6.7 |
|  | Cybonnet | 5 | 3 | 3 | 3.7 |
|  | Wells | 6 | 7 | 6 | 6.7 |

Ratings are based on a scale of 0 to 9 where 0=no symptoms and 9=no grain formation.
Rating Scale:
  0=no damage
  1=81-90% grain develop
  2=71-80% grain develop & 96-100% panicles broken from vertical
  3=61-80% grain develop & 91-95% panicles broken from vertical
  4=41-60% grain develop & 61-90% panicles broken from vertical
  5=21-40% grain develop & 31-60% panicles broken from vertical—appearance of parrot-beak
  6=11-20% grain develop & 10-30% panicles broken from vertical
  7=panicles emerged but totally up right; only 0-10% grain develop
  8=0-10% panicle emergence, no seed produced
  9=no panicles Tables 24, 25, and 26 show the influence of seeding date on grain yield in bushels per acre and milling yield in % Milled Head Rice:% Total Milled Rice (% HR–% TR) of selected rice varieties conducted at the Rice Research Extension Center (RREC) in 2009 (Table 24) and the DD50 in 2009 (Tables 25 & 26).

In Table 24, column 1 shows the variety, columns 2 to 5 show yield for each seeding date and column 6 shows the mean yield for all dates for each variety. Column 7 to 10 shows the milling yield for each seeding date and column eleven shows the mean yield for all dates for each variety.

In Table 25, column 1 shows the variety, columns 2 to 5 show yield for each seeding date and column 6 shows the mean yield for all dates for each variety.

In Table 26, column 1 shows the variety, columns 2 to 5 shows the milling yield for each seeding date and column 6 shows the mean yield for all dates for each variety.

TABLE 24

| | Grain Yield Bushels/acre | | | | | Milling Yield % HR-% TR | | | | |
|---|---|---|---|---|---|---|---|---|---|---|
| Variety | March 30 | April 16 | May 19 | June 16 | Mean | March 30 | April 16 | May 19 | June 16 | Mean |
| Roy J | 179 | 184 | 183 | 97 | 161 | 59-69 | 63-68 | 60-68 | 56-65 | 60-68 |
| Arize QM1003 | 222 | 228 | 193 | 138 | 196 | 57-65 | 63-67 | 45-37 | 50-68 | 54-66 |
| Bowman | 209 | 174 | 145 | 75 | 151 | 58-68 | 65-68 | 40-66 | 27-53 | 47-64 |
| Catahoula | 176 | 165 | 148 | 97 | 146 | 66-73 | 68-72 | 53-63 | 60-67 | 62-69 |
| CL 111 | 204 | 185 | 147 | 111 | 162 | 61-69 | 66-70 | 55-67 | 53-66 | 59-68 |
| CL 131 | 175 | 181 | 160 | 144 | 165 | 66-72 | 68-71 | 59-69 | 59-67 | 63-70 |
| CL 142 | 184 | 176 | 149 | 103 | 153 | 63-72 | 65-71 | 54-69 | 49-63 | 58-69 |
| CL 151 | 231 | 192 | 167 | 124 | 178 | 58-69 | 64-68 | 57-67 | 49-61 | 57-66 |
| CL 171AR | 182 | 161 | 154 | 117 | 153 | 65-71 | 68-71 | 57-69 | 53-65 | 61-69 |
| CL 181 | 198 | 195 | 152 | 126 | 167 | 59-67 | 64-70 | 63-68 | 55-63 | 60-67 |
| Jazzman | 202 | 185 | 127 | 98 | 153 | 64-71 | 66-68 | 61-70 | 52-64 | 61-68 |
| JES | 209 | 177 | 188 | 115 | 172 | 61-69 | 66-69 | 57-68 | 53-67 | 59-68 |
| Neptune | 210 | 216 | 175 | 109 | 178 | 70-72 | 71-73 | 66-71 | 62-67 | 67-71 |
| Rice Tec CL XL729 | 273 | 246 | 183 | 146 | 212 | 61-70 | 65-71 | 61-69 | 55-66 | 60-69 |
| Rice Tec CL XL745 | 240 | 216 | 162 | 121 | 185 | 58-70 | 66-73 | 53-70 | 50-64 | 56-69 |
| Rice Tec XL 723 | 263 | 212 | 201 | 149 | 206 | 61-70 | 67-71 | 65-71 | 47-69 | 60-70 |
| Taggart | 230 | 195 | 165 | 95 | 171 | 60-71 | 65-71 | 60-67 | 41-60 | 56-67 |
| Templeton | 232 | 191 | 167 | 119 | 177 | 62-70 | 67-70 | 57-67 | 39-64 | 57-68 |
| Wells | 215 | 192 | 191 | 135 | 183 | 64-72 | 66-70 | 61-69 | 54-65 | 61-69 |
| Mean | 210 | 193 | 164 | 117 | 171 | 62-70 | 66-70 | 57-68 | 50-64 | 59-68 |

TABLE 25

| | Grain Yields | | | | |
|---|---|---|---|---|---|
| Variety | 30-Mar | 16-Apr | 19-May | 16-Jun | Average |
| Roy J | 179 | 184 | 183 | 97 | 161 |
| Catahoula | 176 | 165 | 148 | 97 | 146 |
| Taggart | 230 | 195 | 165 | 95 | 171 |
| Templeton | 232 | 191 | 167 | 119 | 177 |
| Wells | 215 | 192 | 191 | 135 | 183 |
| Mean | 210 | 193 | 164 | 117 | 171 |
| C.V | 8.9 | 7.6 | | | |
| LSD | 30.9 | 24.2 | | | |

TABLE 26

Milling Yields

| Variety | 30-Mar | 16-Apr | 19-May | 16-Jun | Average |
|---|---|---|---|---|---|
| Roy J | 59-69 | 63-68 | 60-68 | 56-65 | 60-68 |
| Catahoula | 66-73 | 68-72 | 53-63 | 60-67 | 62-69 |
| Taggart | 60-71 | 65-71 | 60-67 | 41-60 | 56-67 |
| Templeton | 62-70 | 67-70 | 57-67 | 39-64 | 57-68 |
| Wells | 64-72 | 66-70 | 61-69 | 54-65 | 61-69 |
| Mean | 62-70 | 66-70 | 57-68 | 50-64 | 59-68 |

Table 27 shows the influence of seeding date on days from emergence to one-half inch internode elongation and 50% heading for selected rice varieties in seeding date studies conducted at the RREC during 2008. Column 1 shows the variety, columns 2 to 5 show the number of days after emergence for each seeding date and column 6 shows the mean for the number of days after emergence for each variety for all seeding dates. Columns 7 to 10 show the days to 50% heading in days after emergence for each seeding date and column eleven shows the mean for the days to 50% heading in days after emergence of each variety for all seeding dates.

Table 28 shows the influence of seeding date to the beginning of internode elongation, studies conducted at the RREC during 2009. Column 1 shows the variety, columns 2, 4, 6, and 8 show the days to beginning elongation, columns 3, 5, 7, and 9 show the degree day 50 (DD50) in units for columns 2, 4, 6 and 8, respectively. Columns 10 and 11 show the averages of all seeding dates.

Table 29 shows the influence of seeding date to one-half inch internode elongation, studies conducted at the RREC during 2009. Column 1 shows the variety, columns 2, 4, 6, and 8 show the days to emergence to one-half inch internode elongation, columns 3, 5, 7, and 9 show the degree day 50 (DD50) in units for columns 2, 4, 6 and 8, respectively. Columns 10 and 11 show the averages of all seeding dates.

TABLE 27

| | Days to ½" Internode Elongation | | | | | Days to 50% Heading | | | | |
|---|---|---|---|---|---|---|---|---|---|---|
| Variety | March 26 | April 17 | May 19 | June 12 | Mean | March 26 | April 17 | May 19 | June 12 | Mean |
| | days after emergence | | | | | days after emergence | | | | |
| Roy J | 65 | 66 | 51 | 44 | 56 | 96 | 102 | 82 | 79 | 90 |
| Arize QM1003 | 60 | 58 | 44 | 37 | 50 | 96 | 101 | 82 | 78 | 89 |
| Bowman | 66 | 68 | 54 | 45 | 58 | 91 | 96 | 80 | 75 | 86 |
| Catahoula | 59 | 57 | 45 | 37 | 49 | 89 | 97 | 76 | 68 | 83 |
| CL 111 | 58 | 57 | 44 | 37 | 49 | 87 | 90 | 79 | 72 | 82 |
| CL 131 | | | | | | 83 | 90 | 78 | 72 | 81 |
| CL 142 | 61 | 61 | 48 | 44 | 53 | 88 | 92 | 80 | 76 | 84 |
| CL 151 | 57 | 56 | 44 | 40 | 49 | 83 | 89 | 80 | 76 | 82 |
| CL 171AR | | | | | | 89 | 98 | 81 | 76 | 86 |
| CL 181 | 61 | 59 | 49 | 42 | 53 | 88 | 95 | 81 | 75 | 85 |
| Jazzman | 67 | 65 | 52 | 47 | 58 | 89 | 94 | 80 | 76 | 85 |
| JES | 63 | 62 | 48 | 40 | 53 | 93 | 98 | 81 | 78 | 87 |
| Neptune | 67 | 68 | 55 | 50 | 60 | 93 | 93 | 80 | 78 | 86 |
| Rice Tec CL XL729 | | | | | | 84 | 89 | 83 | 76 | 83 |
| Rice Tec CL XL745 | 57 | 57 | 47 | 41 | 50 | 82 | 85 | 78 | 71 | 79 |
| Rice Tec XL 723 | 60 | 57 | 46 | 40 | 51 | 87 | 90 | 82 | 74 | 83 |
| RU0701124 | 55 | 55 | 40 | 32 | 45 | 78 | 80 | 70 | 61 | 72 |
| Taggart | 64 | 64 | 50 | 43 | 55 | 93 | 99 | 82 | 77 | 88 |
| Templeton | 62 | 63 | 50 | 43 | 55 | 92 | 99 | 83 | 78 | 88 |
| Wells | 61 | 63 | 50 | 44 | 55 | 89 | 96 | 80 | 76 | 85 |
| Mean | 83 | 61 | 48 | 41 | 53 | 89 | 94 | 80 | 75 | 84 |

TABLE 28

Beginning Internode Elongation

| | Mar. 30, 2009 | | Apr. 16, 2009 | | May 19, 2009 | | Jun. 16, 2009 | | Average | |
|---|---|---|---|---|---|---|---|---|---|---|
| Variety | DAYS | DD50 UNITS | DAYS | DD50 UNITS | DAYS | DD50 UNITS | DAYS | DD50 UNITS | DAYS | DD50 UNITS |
| Roy J | 60 | 1351 | 57 | 1387 | 44 | 1277 | 37 | 1071 | 50 | 1272 |
| Catahoula | 55 | 1198 | 51 | 1185 | 38 | 1098 | 29 | 874 | 43 | 1089 |
| Taggart | 57 | 1266 | 55 | 1323 | 43 | 1235 | 36 | 1043 | 48 | 1217 |
| Templeton | 58 | 1276 | 56 | 1345 | 43 | 1246 | 36 | 1043 | 48 | 1227 |
| Wells | 57 | 1255 | 56 | 1345 | 43 | 1235 | 36 | 1053 | 48 | 1222 |
| Mean | 55.7 | 1217.7 | 54.1 | 1282.9 | 41.3 | 1193.8 | 34.1 | 1000.2 | 46.3 | 1173.7 |
| C.V | 3.7 | 5.0 | 1.1 | 1.4 | 1.9 | 2.0 | 2.9 | 2.8 | | |
| LSD | 3.4 | 101.6 | 1.0 | 30.3 | 1.3 | 38.9 | 1.6 | 46.3 | | |

TABLE 29

| | ½" Internode Elongation | | | | | | | | |
|---|---|---|---|---|---|---|---|---|---|
| | Mar. 30, 2009 | | Apr. 16, 2009 | | May 19, 2009 | | Jun. 16, 2009 | | Average | |
| Variety | DAYS | DD50 UNITS | DAYS | DD50 UNITS | DAYS | DD50 UNITS | DAYS | DD50 UNITS | DAYS | DD50 UNITS |
| Roy J | 65 | 1500 | 66 | 1643 | 51 | 1482 | 44 | 1264 | 56 | 1472 |
| Catahoula | 59 | 1308 | 57 | 1366 | 45 | 1309 | 37 | 1080 | 49 | 1266 |
| Taggart | 64 | 1479 | 64 | 1582 | 50 | 1458 | 43 | 1245 | 55 | 1441 |
| Templeton | 62 | 1426 | 63 | 1561 | 50 | 1448 | 43 | 1244 | 55 | 1420 |
| Wells | 61 | 1394 | 63 | 1572 | 50 | 1448 | 44 | 1272 | 55 | 1421 |
| Mean | 61 | 1394 | 61 | 1497 | 48 | 1394 | 41 | 1203 | 53 | 1372 |
| C.V | 1.9 | 2.6 | 1.5 | 2.0 | 1.9 | 1.9 | 2.4 | 3.0 | | |
| LSD | 1.9 | 60.4 | 1.6 | 48.6 | 1.5 | 43.4 | 1.6 | 46.0 | | |

Table 30 shows the influence of nitrogen (N) fertilizer rate on the grain yield of Arkansas experimental rice variety Roy J at the Rice Research and Extension Center near Stuttgart, Ark., during 2009. $^z$A bushel of rice weighs 45 lb.

TABLE 30

| N Fertilizer Rate (lbs N/A) | Grain Yield (bushels/acre$^z$) |
|---|---|
| 0 | 109 |
| 60 | 169 |
| 90 | 188 |
| 120 | 191 |
| 150 | 196 |
| 180 | 194 |
| LSD$_{(\alpha=0.05)}$ | 12.4 |
| C.V. (%) | 4.705 |

DEPOSIT INFORMATION

A deposit of the BOARD OF TRUSTEES OF THE UNIVERSITY OF ARKANSAS, N.A. proprietary RICE CULTIVAR ROY J disclosed above and recited in the appended claims has been made with the American Type Culture Collection (ATCC), 10801 University Boulevard, Manassas, Va. 20110. The date of deposit was Jan. 25, 2011. The deposit of 2,500 seeds was taken from the same deposit maintained by BOARD OF TRUSTEES OF THE UNIVERSITY OF ARKANSAS, N.A. since prior to the filing date of this application. All restrictions will be irrevocably removed upon granting of a patent, and the deposit is intended to meet all of the requirements of 37 C.F.R. §§1.801-1.809. The ATCC Accession Number is PTA-11606. The deposit will be maintained in the depository for a period of thirty years, or five years after the last request, or for the enforceable life of the patent, whichever is longer, and will be replaced as necessary during that period.

What is claimed is:

1. A seed of rice cultivar Roy J, wherein a representative sample of seed of said cultivar was deposited under ATCC Accession No. PTA-11606.

2. A rice plant, or a part thereof, produced by growing the seed of claim 1.

3. A tissue culture produced from the protoplasts or cells from the plant of claim 2, wherein said cells or protoplasts are produced from a plant part selected from the group consisting of leaves, pollen, embryos, cotyledon, hypocotyl, meristematic cells, roots, root tips, pistils, anthers, flowers, stems, glumes and panicles.

4. A rice plant regenerated from the tissue culture of claim 3, wherein said rice plant has all of the physiological and morphological characteristics of rice cultivar Roy J listed in Table 1.

5. A method for producing a rice seed, said method comprising crossing two rice plants and harvesting the resultant rice seed, wherein at least one rice plant is the rice plant of claim 2.

6. A rice seed produced by the method of claim 5.

7. A rice plant, or a part thereof, produced by growing said seed of claim 6.

8. The method of claim 5, wherein one of said rice plants is rice cultivar Roy J and the other is transgenic.

9. A method of producing an herbicide resistant rice plant, wherein said method comprises introducing a gene conferring herbicide resistance into the rice plant of claim 2.

10. An herbicide resistant rice plant produced by the method of claim 9, wherein the gene confers resistance to an herbicide selected from the group consisting of dicamba, phenoxy proprionic acid, cyclohexone, cyclohexanedione, imidazolinone, sulfonylurea, glyphosate, glufosinate, L-phosphinothricin, triazine and benzonitrile.

11. A method of producing a pest or insect resistant rice plant, wherein said method comprises introducing a gene conferring pest or insect resistance into the rice plant of claim 2.

12. A pest or insect resistant rice plant produced by the method of claim 11.

13. The rice plant of claim 12, wherein the gene encodes a *Bacillus thuringiensis* endotoxin.

14. A method of producing a disease resistant rice plant, wherein the method comprises introducing a gene which confers disease resistance into the rice plant of claim 2.

15. A disease resistant rice plant produced by the method of claim 14.

16. A method of producing a rice plant with modified fatty acid metabolism or modified carbohydrate metabolism, wherein the method comprises introducing a gene encoding a protein selected from the group consisting of phytase, fructosyltransferase, levansucrase, alpha-amylase, invertase and starch branching enzyme or DNA encoding an antisense of stearyl-ACP desaturase into the rice plant of claim 2.

17. A rice plant having modified fatty acid metabolism or modified carbohydrate metabolism produced by the method of claim 16.

18. A method of introducing a desired trait into rice cultivar Roy J wherein the method comprises:
   (a) crossing a Roy J plant, wherein a representative sample of seed was deposited under ATCC Accession No. PTA-11606, with a plant of another rice cultivar that comprises a desired trait to produce progeny plants, wherein the desired trait is selected from the group consisting of male sterility, herbicide resistance, insect resistance, modified fatty acid metabolism, modified carbohydrate metabolism and resistance to bacterial disease, fungal disease or viral disease;
(b) selecting one or more progeny plants that have the desired trait;
(c) backcrossing the selected progeny plants with the Roy J plants to produce backcross progeny plants;
(d) selecting for backcross progeny plants that have the desired trait; and
(e) repeating steps (c) and (d) three times to produce selected fourth or higher backcross progeny plants that comprise the desired trait and all of the physiological and morphological characteristics of rice cultivar Roy J as listed in Table 1.

19. A rice plant produced by the method of claim 18, wherein the plant has the desired trait and all of the physiological and morphological characteristics of rice cultivar Roy J as listed in Table 1.

20. The rice plant of claim 19, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

21. The rice plant of claim 19, wherein the desired trait is insect resistance and the insect resistance is conferred by a gene encoding a *Bacillus thuringiensis* endotoxin.

22. The plant of claim 19, wherein the desired trait is modified fatty acid metabolism or modified carbohydrate metabolism and said desired trait is conferred by a nucleic acid encoding a protein selected from the group consisting of phytase, fructosyltransferase, levansucrase, alpha-amylase, invertase and starch branching enzyme or DNA encoding an antisense of stearyl-ACP desaturase.

* * * * *